(12) United States Patent
Hamada et al.

(10) Patent No.: US 10,682,330 B2
(45) Date of Patent: Jun. 16, 2020

(54) METHOD FOR PRODUCING LIPOSOME ENCAPSULATING PACLITAXEL MONOGLYCOSIDE AND/OR DOCETAXEL MONOGLYCOSIDE

(71) Applicants: ENSUIKO SUGAR REFINING CO., LTD., Tokyo (JP); Hiroki Hamada, Okayama (JP); Ichiro Fujiwara, Okayama (JP); NATIONAL UNIVERSITY CORPORATION OKAYAMA UNIVERSITY, Okayama-shi, Okayama (JP)

(72) Inventors: Hiroki Hamada, Okayama (JP); Ichiro Fujiwara, Okayama (JP); Masaharu Seno, Okayama (JP); Tomonari Kasai, Okayama (JP); Tsukasa Shigehiro, Okayama (JP); Masaharu Murakami, Okayama (JP); Katsuhiko Mikuni, Kanagawa (JP)

(73) Assignees: ENSUIKO SUGAR REFINING CO., LTD., Tokyo (JP); HIROKI HAMADA, Okayama (JP); YOSHIO SHIMIZU, Okayama (JP); NATIONAL UNIVERSITY CORPORATION OKAYAMA UNIVERSITY, Okayama (JP)

(*) Notice: Subject to any disclaimer, the term of this patent is extended or adjusted under 35 U.S.C. 154(b) by 225 days.

(21) Appl. No.: 14/386,855

(22) PCT Filed: Mar. 22, 2013

(86) PCT No.: PCT/JP2013/058242
§ 371 (c)(1),
(2) Date: Sep. 22, 2014

(87) PCT Pub. No.: WO2013/141346
PCT Pub. Date: Sep. 26, 2013

(65) Prior Publication Data
US 2015/0056270 A1 Feb. 26, 2015
US 2016/0256566 A2 Sep. 8, 2016

(30) Foreign Application Priority Data

Mar. 22, 2012 (JP) ................................. 2012-065743

(51) Int. Cl.
| | | |
|---|---|---|
| *A61K 31/337* | (2006.01) | |
| *A61K 47/26* | (2006.01) | |
| *A61K 9/127* | (2006.01) | |
| *A61K 31/7048* | (2006.01) | |
| *C07K 16/32* | (2006.01) | |
| *A61K 47/69* | (2017.01) | |
| *A61K 39/00* | (2006.01) | |

(52) U.S. Cl.
CPC ............ *A61K 31/337* (2013.01); *A61K 9/127* (2013.01); *A61K 31/7048* (2013.01); *A61K 47/6913* (2017.08); *C07K 16/32* (2013.01); *A61K 2039/505* (2013.01); *C07K 2317/24* (2013.01); *C07K 2317/73* (2013.01)

(58) Field of Classification Search
None
See application file for complete search history.

(56) References Cited

U.S. PATENT DOCUMENTS

| | | | |
|---|---|---|---|
| 5,767,297 A | 6/1998 | Mandai et al. | |
| 6,306,893 B1 * | 10/2001 | Mandai | C07H 15/04 514/449 |
| 7,361,683 B2 * | 4/2008 | Lee | A61K 9/0019 514/449 |
| 2008/0206139 A1 * | 8/2008 | Connor | A61K 9/0019 424/9.1 |

(Continued)

FOREIGN PATENT DOCUMENTS

| | | | |
|---|---|---|---|
| CN | 102552123 A | * | 7/2012 |
| EP | 1022284 | | 7/2000 |
| JP | 09-286794 | | 11/1997 |

(Continued)

OTHER PUBLICATIONS

CN102552123A Google translation.*
Yang et al ("Yang II", Int. J. Pharmaceutics, 2007, 338, 317-326) (Year: 2007).*
Murakami, M. et al., Encapsulation of glycosylated paclitaxel into liposome targeting Her2, Journal of Japanese Biochemical Society, 2010, Abstract, No. 3, p. 1235.
Yang, T. et al., Antitumor effect of paclitaxel-loaded PEGylated immunoliposomes against human breast cancer cells, Pharmaceutical Research, 2007, vol. 24, No. 12, pp. 2402-2411.
Shimoda, K. et al., Chemo-enzymatic synthesis of ester-linked taxol-oligosaccharide conjugates as potential prodrugs, Tetrahedron Letters, 2008, vol. 49, pp. 601-604.

(Continued)

*Primary Examiner* — Mark Halvorson
*Assistant Examiner* — Kauser M Akhoon
(74) *Attorney, Agent, or Firm* — Wenderoth, Lind & Ponack LLP

(57) ABSTRACT

In order to reduce the side effects of paclitaxel derivatives having excellent anti-cancer effects, an attempt was made to produce a liposome encapsulating paclitaxel derivatives such as paclitaxel monoglycosides and docetaxel monoglycosides. However, the introduction efficiency of paclitaxel derivatives, etc., into a liposome was poor, and this technique was not developed to a practical level. The present invention provides a method for producing a liposome encapsulating a paclitaxel monoglycoside and/or a docetaxel monoglycoside, and having an antibody specifically recognizing a cancer cell, the method comprising a step of bringing a liposome encapsulating a polyoxyethylene ester derivative, a lower alcohol, and a buffer or water into contact with a solution in which a paclitaxel monoglycoside and/or a docetaxel monoglycoside is dissolved in an alkylene glycol-containing buffer or water.

9 Claims, 10 Drawing Sheets

(56) References Cited

U.S. PATENT DOCUMENTS

2010/0034874 A1 2/2010 Hirai et al.
2013/0011466 A1 1/2013 Hirai et al.

FOREIGN PATENT DOCUMENTS

| JP | 2006-265152 | 10/2006 | |
|----|----|----|----|
| JP | 2009-132629 | 6/2009 | |
| WO | WO 9723208 A1 * | 7/1997 | ........... A61K 9/0019 |
| WO | 1999/018113 | 4/1999 | |
| WO | 1999/022759 | 5/1999 | |
| WO | 2008/072584 | 6/2008 | |

OTHER PUBLICATIONS

Mikuni, K. et al., In vivo antitumor activity of novel water-soluble taxoids, Biological and Pharmaceutical Bulletin, 2008, vol. 31, No. 6, pp. 1155-1158.
International Search Report for PCT/JP2013/058242, dated Jun. 11, 2013.
Extended European Search Report dated Oct. 5, 2015 in corresponding European Application No. 13764209.6.
Shigehiro, Tsukasa et al., "Efficient Drug Delivery of Paclitaxel Glycoside: A Novel Solubility Gradient Encapsulation into Liposomes Couples with Immunoliposomes Preparation", *PLOS One*, 2014, vol. 9, No. 9, pp. 1-10.

* cited by examiner

METHOD FOR PRODUCING LIPOSOME ENCAPSULATING PACLITAXEL MONOGLYCOSIDE AND/OR DOCETAXEL MONOGLYCOSIDE

TECHNICAL FIELD

The present invention relates to a method for producing a liposome encapsulating a paclitaxel monoglycoside and/or a docetaxel monoglycoside.

BACKGROUND ART

Many anti-cancer drugs have a mechanism of inhibiting the division of cancer cells, whose growth control breaks down. Since such anti-cancer drugs exhibit extremely effective anti-cancer functions, they are valuable in use; however, the anti-cancer drugs also exhibit a cell-growth inhibiting function on normal cells, which causes many side effects and thus often prevents its use.

For this reason, anti-cancer drugs have required DDS techniques that specifically deliver drugs to cancer cells without acting on normal cells. To reduce side effects, various anti-cancer drugs are combined with DDS techniques, and developed. One preferably used DDS technique is a technique using a liposome comprising a lipid bilayer membrane.

For example, a technique using a liposome and a platinum anti-cancer agent such as oxaliplatin, cisplatin, or carboplatin has been developed (PTL 1). To introduce such an anti-cancer drug using a remote loading method, only a weakly basic anti-cancer drug can be used. To solve this problem, a remote loading method utilizing a solubility gradient has been developed; however, this method only applies to highly water-soluble drugs, and the introduction efficiencies of these drugs are very low (PTL 2).

On the other hand, paclitaxel, docetaxel, etc., which have been applied to breast cancers, cervical cancers, etc., are practically insoluble in water; therefore, they are prepared at the time of use by dissolving them in a solvent such as alcohol, and then administered. This, however, requires time, and involves risk.

For the purpose of improving the solubility of paclitaxel, docetaxel, etc., in water, various paclitaxel derivatives have been produced. For example, as shown in NPL 1, a technique of adding a monosaccharide such as glucose, galactose, mannose, xylose, or the like, to paclitaxel has been developed.

Unfortunately, even such paclitaxel derivatives, e.g., paclitaxel monoglycosides and docetaxel monoglycosides do not have sufficient water solubility, and there has been no knowledge of a DDS formulation obtained by combining paclitaxel derivatives and a liposome.

CITATION LIST

Patent Literature

PTL 1: WO2008/072584
PTL 2: JP2009-132629A

Non-Patent Literature

NPL 1: Biol. Pharm. Bull. 2008 June; 31(6): 1155-8

SUMMARY OF INVENTION

Technical Problem

In order to reduce the side effects of paclitaxel derivatives having excellent anti-cancer functions, an attempt was made to produce a liposome encapsulating paclitaxel derivatives such as paclitaxel monoglycosides and docetaxel monoglycosides. However, the introduction efficiency of paclitaxel derivatives, etc., into a liposome was poor, and this technique was not developed to a practical level.

Solution to Problem

To solve the above problem, the present inventors conducted extensive research. Consequently, they found that to efficiently introduce paclitaxel derivatives such as docetaxel monoglycosides and paclitaxel monoglycosides into a liposome, the paclitaxel derivatives and liposome constituent lipids are mixed in the presence of solvent components in a specific ratio.

The inventors also found that by including a mixed solvent for dissolving paclitaxel derivatives in a liposome beforehand, a paclitaxel monoglycoside, a docetaxel monoglycoside, etc., can be encapsulated in the liposome with high efficiency.

The inventors further found that a liposome encapsulating a paclitaxel monoglycoside, a docetaxel monoglycoside, etc., obtained by the above method has an excellent effect as a DDS. The present invention was accomplished based on the above findings, and broadly includes the following embodiments.

Item 1

A method for producing a liposome encapsulating a paclitaxel monoglycoside and/or a docetaxel monoglycoside, the method comprising a step of performing a liposome formation treatment on a mixture containing a paclitaxel monoglycoside and/or a docetaxel monoglycoside, a polyoxyethylene ester derivative, a lower alcohol, liposome constituent lipids, and a buffer or water, the paclitaxel monoglycoside and/or the docetaxel monoglycoside being contained in an amount of 1500 to less than 3000 wt % based on the total volume of the mixture, the polyoxyethylene ester derivative being contained in an amount of 0.1 to 0.2 part by volume, and the lower alcohol being contained in an amount of 0.1 to 0.2 part by volume, per part by volume of the buffer or water, the paclitaxel monoglycoside and/or docetaxel monoglycoside being encapsulated in an amount of 0.1 to 2.5 parts by weight per part by weight of the total liposome constituent lipids.

Item 2

The method according to Item 1, wherein the liposome formation treatment is any of a thin-film hydration method, freeze-dry method, droplet method, AC-electric field-dependent electroformation method, ultrasonic method, reverse-phase evaporation method, bubbling method, spray-dry method, method using a $CO_2/H_2O$ emulsion, and method using a microchannel.

Item 3

The method according to Item 1 or 2, wherein the glycoside is at least one member selected from the group consisting of glucoside, galactoside, mannoside, xyloside, fructoside, rhamnoside, arabinoside, alloside, altroside, idoside, N-acetylglucosaminide, N-acetylgalactosaminide, taloside, glucuronide, glucosaminide, galactosaminide, and fucoside.

Item 4

The method according to any one of Items 1 to 3, wherein the paclitaxel monoglycoside is 7-α-glucosyloxyacetylpaclitaxel.

Item 5

The method according to any one of Items 1 to 4, wherein the polyoxyethylene ester derivative is polyoxyethylene castor oil ester.

Item 6

The method according to any one of Items 1 to 5, wherein the polyoxyethylene castor oil ester is Cremophor® EL.

Item 7

A liposome formulation encapsulating a solution liquid of paclitaxel monoglycoside and/or docetaxel monoglycoside, and has an antibody specifically recognizing a cancer cell.

Item 8

The liposome formulation according to Item 7, wherein the solution liquid of paclitaxel monoglycoside and/or docetaxel monoglycoside is a solution liquid in which paclitaxel and/or docetaxel monoglycoside is dissolved in a mixed solvent containing a polyoxyethylene ester derivative, a lower alcohol, and a buffer or water.

Item 9

The liposome formulation according to Item 7 or 8, wherein the glycoside is at least one member selected from the group consisting of glucoside, galactoside, mannoside, xyloside, fructoside, rhamnoside, arabinoside, alloside, altroside, idoside, N-acetylglucosaminide, N-acetylgalactosaminide, taloside, glucuronide, glucosaminide, galactosaminide, and fucoside Item 10

The liposome formulation according to any one of Items 7 to 9, wherein the paclitaxel monoglycoside is 7-α-glucosyloxyacetylpaclitaxel.

Item 11

The liposome formulation according to any one of Items 7 to 10, wherein the polyoxyethylene ester derivative is polyoxyethylene castor oil ester.

Item 12

The liposome formulation according to any one of Items 7 to 11, wherein the polyoxyethylene castor oil ester is Cremophor® EL.

Item 13

The liposome formulation according to any one of Items 7 to 12, wherein the liposome contains DPPC and cholesterol in a material quantity ratio of 3:0.5 to 3.

Item 14

The liposome formulation according to any one of Items 7 to 15, wherein the mol of the paclitaxel monoglycoside per mol of the total lipids of the liposome is 1.0 to $15.5 \times 10^{-2}$.

Item 17

The liposome formulation according to any one of Items 7 to 16, wherein the cancer cell is a breast cancer cell.

Item 18

The liposome formulation according to any one of Items 7 to 17, wherein the antibody specifically binds to HER2 protein.

The present invention further includes the following embodiments.

Item I

A method for producing a liposome encapsulating a paclitaxel monoglycoside and/or a docetaxel monoglycoside, and having an antibody specifically recognizing a cancer cell, the method comprising a step of bringing a liposome encapsulating a polyoxyethylene ester derivative, a lower alcohol, and a buffer or water into contact with a solution in which a paclitaxel monoglycoside and/or a docetaxel monoglycoside is dissolved in an alkylene glycol-containing buffer or water.

Item II

The method according to Item I, wherein the solution in which the paclitaxel monoglycoside and/or docetaxel monoglycoside is dissolved is a solution dissolved in an alkylene glycol-containing buffer or water.

Item III

The method according to Item I or II, wherein the glycoside is at least one member selected from the group consisting of glucoside, galactoside, mannoside, xyloside, fructoside, rhamnoside, arabinoside, alloside, altroside, idoside, N-acetylglucosaminide, N-acetylgalactosaminide, taloside, glucuronide, glucosaminide, galactosaminide, and fucoside Item IV The method according to any one of Items I to III, wherein the paclitaxel monoglycoside is 7-α-glucosyloxyacetylpaclitaxel.

Item V

The method according to any one of Items I to IV, wherein the polyoxyethylene ester derivative is polyoxyethylene castor oil ester.

Item VI

The method according to any one of Items I to V, wherein the polyoxyethylene castor oil ester is Cremophor® EL.

Item VII

The method according to any one of Items I to VI, wherein the liposome contains DPPC and cholesterol in a material quantity ratio of 3:0.5 to 3.

Item VIII

The method according to any one of Items I to VII, wherein the contact time is 5 to 60 minutes.

Item IX

The method according to any one of Items I to VIII, wherein the cancer cell is a breast cancer cell.

Item X

The method according to any one of Items I to IX, wherein the antibody specifically binds to HER2 protein.

Advantageous Effects of Invention

According to the method of the present invention, a paclitaxel monoglycoside and/or a docetaxel monoglycoside can be efficiently encapsulated in a liposome. Further, an antibody specifically recognizing a cancer cell can be bound to the liposome encapsulating a paclitaxel monoglycoside and/or a docetaxel monoglycoside obtained by the method of the present invention. The liposome having such an antibody, which is obtained by the production method of the present invention, is very useful as a DDS.

DESCRIPTION OF EMBODIMENTS

Liposome Production Method

Figure 1:
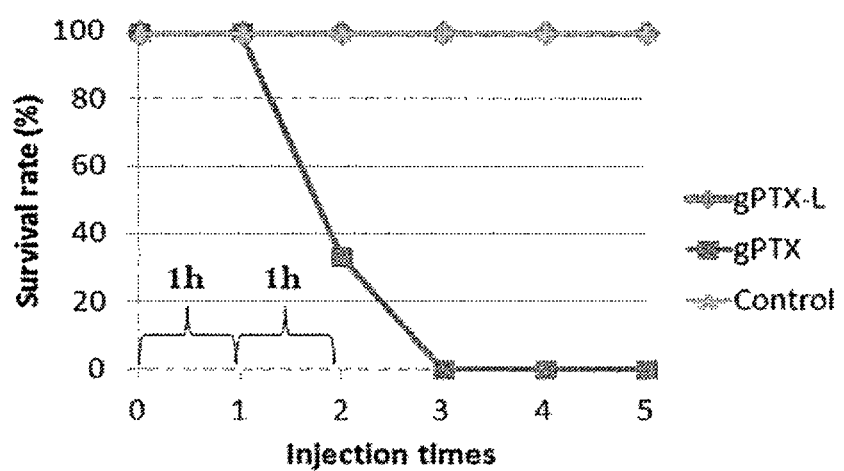
FIG. 1 shows acute toxicity study results in Test Example 4. In the graph, the vertical axis indicates the survival rate, and the horizontal axis indicates the number of administrations.

The method for producing a liposome encapsulating a paclitaxel monoglycoside and/or a docetaxel monoglycoside, which is one of the embodiments of the liposome production method of the present invention (hereinafter sometimes referred to as "first embodiment production method"), comprises the step of performing a liposome formation treatment on a mixture containing a paclitaxel monoglycoside and/or a docetaxel monoglycoside, a polyoxyethylene ester derivative, a lower alcohol, liposome constituent lipids, and a buffer or water.

The method may comprise the steps of: preparing a solution containing a paclitaxel monoglycoside and/or a docetaxel monoglycoside, a polyoxyethylene ester derivative, a lower alcohol, and a buffer or water beforehand; mixing the solution with liposome constituent lipids; and then subjecting the mixture to a liposome formation treatment.

In another embodiment, a solution containing a paclitaxel monoglycoside and/or a docetaxel monoglycoside, a polyoxyethylene ester derivative, and a lower alcohol may be prepared, and mixed with a mixture containing liposome constituent lipids and a buffer or water; the mixture may then be subjected to a liposome formation treatment.

Specifically, the order of mixing lipids with a paclitaxel monoglycoside and/or a docetaxel monoglycoside is not limited; however, the amount of paclitaxel monoglycoside and/or docetaxel monoglycoside relative to the total volume of paclitaxel monoglycoside and/or docetaxel monoglycoside, polyoxyethylene ester derivative, lower alcohol, and buffer or water is about 1500 to less than 3000, preferably about 1700 to less than 2500, and more preferably about 1800 to 2200 wt %.

The amount of polyoxyethylene ester derivative used is about 0.1 to 0.2, preferably about 0.12 to 0.19, and more preferably about 0.13 to 0.18 part by volume per part by volume of buffer or water.

The amount of lower alcohol used is about 0.1 to 0.2, preferably 0.12 to 0.19, and more preferably about 0.13 to 0.18 part by volume per part by volume of buffer or water.

The term "part by volume" used in the present specification is the numerical value obtained by measurement at normal pressure and in a room-temperature environment.

Although examples of the polyoxyethylene ester derivative are not particularly limited, they include sodium polyoxyethylene alkyl ether sulfate, polyoxyethylene alkyl ether phosphate, polyoxyethylene alkyl phenyl ether phosphate, poly(oxyethylene-oxypropylene)methylpolysiloxane copolymer, polyoxyethylene octyl phenyl ether, polyoxyethylene stearylether, polyoxyethylene stearic acid amide, polyoxyethylene cetylether, polyoxyethylene polyoxypropylene glycol, polyoxyethylene castor oil ester, etc.

Of these, polyoxyethylene castor oil ester is preferable, and polyoxyethylene (C24) castor oil ester (Cremophor® EL) is more preferable.

Although the lower alcohol is not particularly limited, it is generally a $C_{1-4}$ alcohol.

Although the buffer is not particularly limited, examples include PBS, MES, ADA, PIPES, ACES, cholamine chloride, BES, TES, HEPES, citric acid, boric acid, tartaric acid, etc.

Examples of the liposome constituent lipids include phospholipids, cholesterols, fatty acids, etc. Specific examples of the phospholipids include phosphatidylcholine, phosphatidylserine, phosphatidylglycerol, phosphatidylinositol, phosphatidylethanolamine, phosphatidic acid, cardiolipin, sphingomyelin, egg yolk lecithin, soy lecithin, lysolecithin, and natural phospholipids obtained by hydrogenating the above according to an ordinal method; distearoyl phosphatidylcholine, dipalmitoylphosphatidylcholine (DPPC), dipalmitoylphosphatidylethanolamine (DPPE), dithiodipyridine-dipalmitoylphosphatidylethanolamine (DTP-DPPE), dipalmitoylphosphatidylglycerol (DPPG), dipalmitoylphosphatidylserine (DPPS), eleostearoylphosphatidylcholine, eleostearoylphosphatidylethanolamine, eleostearoylphosphatidylserine, and like synthetic phospholipids; etc.

The above-described phospholipids, cholesterols, and fatty acids may be suitably modified. Although the modification is not particularly limited, examples include modification by a polyalkylene glycol such as polyethylene glycol or polypropylene glycol. These phospholipids may be suitably used in combination.

Examples of the cholesterol include cholesterol, phytosterol, etc.

Examples of the fatty acids include oleic acid, palmitoleic acid, linoleic acid, fatty acid mixtures containing these unsaturated fatty acids, etc. Of these, a liposome containing an unsaturated fatty acid with short side chains is useful for producing a liposome with a small particle size in view of curvature relationship.

The liposome obtained by the first embodiment production method of the present invention encapsulates a paclitaxel monoglycoside and/or a docetaxel monoglycoside.

The term "encapsulate" used in the present specification means that the liposome may completely include a paclitaxel monoglycoside and/or a docetaxel monoglycoside; however, the term "encapsulate" also indicates the state where a paclitaxel monoglycoside molecule and/or a docetaxel monoglycoside molecule penetrates a lipid bilayer membrane forming the liposome. In the specification, the term "enclose" is sometimes used in the same meaning as "encapsulate."

The liposome obtained by the first embodiment production method of the present invention encapsulates a paclitaxel monoglycoside and/or a docetaxel monoglycoside in an amount of about 0.1 to 2.5, preferably about 1.3 to 2.4, and more preferably about 1.6 to 2.3 parts by weight per part by weight of the total lipids.

The paclitaxel monoglycoside and docetaxel monoglycoside are respectively obtained by adding a monosaccharide to paclitaxel or docetaxel. The position at which a monosaccharide is added to the paclitaxel is not particularly limited; however, the monosaccharide may be, for example, added at position 10 or 7 of the taxane ring of the paclitaxel. is known to exist in nature, and a monosaccharide is preferably added at position 7 from the viewpoint of binding stability.

The position at which a monosaccharide is added to the docetaxel is also not particularly limited; however, the monosaccharide may be, for example, added at position 10 or 7 of the taxane ring of the docetaxel.

Although the monosaccharide is not particularly limited, examples include glucose, galactose, mannose, xylose, fructose, rhamnose, arabinose, allose, altrose, idose, N-acetylglucosamine, N-acetylgalactosamine, talose, glucuronic acid, glucosamine, galactosamine, fucose, etc. Of these, from the viewpoint of preventing excessive loss of the anti-cancer effects of paclitaxel and docetaxel, glucose, galactose, mannose, xylose, etc., are preferably used.

Examples of the glycoside in the paclitaxel monoglycoside and docetaxel monoglycoside of the present invention include glucoside, galactoside, mannoside, xyloside, fructoside, rhamnoside, arabinoside, alloside, altroside, idoside, N-acetylglucosaminide, N-acetylgalactosaminide, taloside, glucuronides, glucosaminide, galactosaminide, fucoside, etc.

The paclitaxel monoglycoside or docetaxel monoglycoside may further include a group between the monosaccharide and the paclitaxel, or between the monosaccharide and the docetaxel. For example, a $C_1$-$C_8$ alkanoyl group, etc., is one example.

Specifically, in the paclitaxel monoglycoside or docetaxel monoglycoside mentioned above, the hydrogen atom of the hydroxyl group at position 7 or 10 of the taxane ring of the paclitaxel or docetaxel may be substituted by a $C_{1-8}$ alkanoyloxy group, which has been substituted by the monosaccharide.

The paclitaxel before monosaccharide addition may be a known paclitaxel derivative. The paclitaxel derivatives described in JPH08-73449A, JPH07-233159A, etc., can also be listed.

The most preferable paclitaxel monoglycoside is 7-α-glucosyloxyacetylpaclitaxel, represented by formula (1) below.

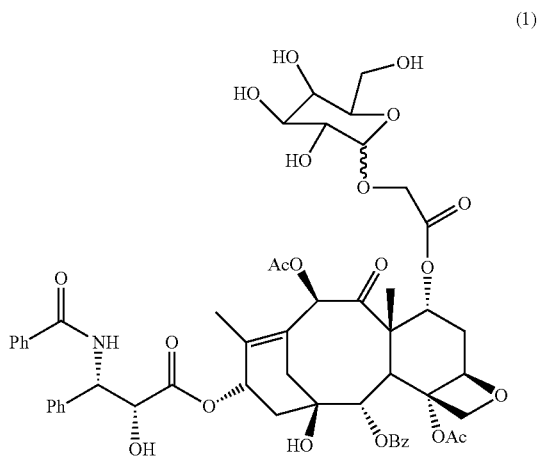

(1)

The paclitaxel monoglycoside can be produced by a known method, for example, with reference to the method described in NPL1. Specifically, an intended monosaccharide to be added to the paclitaxel is acetylated beforehand, and then the acetylated product is esterified at position 7 or 10 of the taxane ring of the paclitaxel, as described above, thus adding the sugar chain.

The most preferable docetaxel monoglycosides are docetaxel monoglycosides represented by formulae (2) to (4) below.

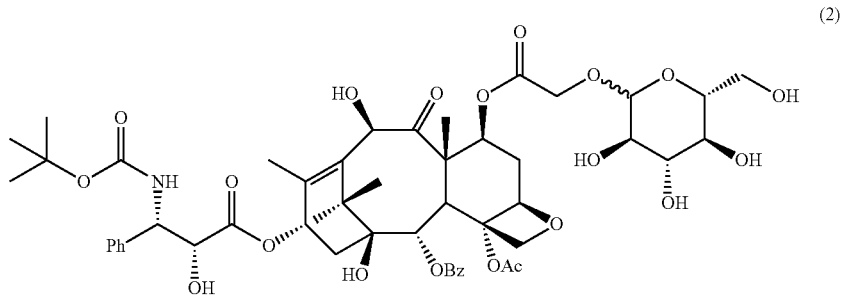

(2)

(3)

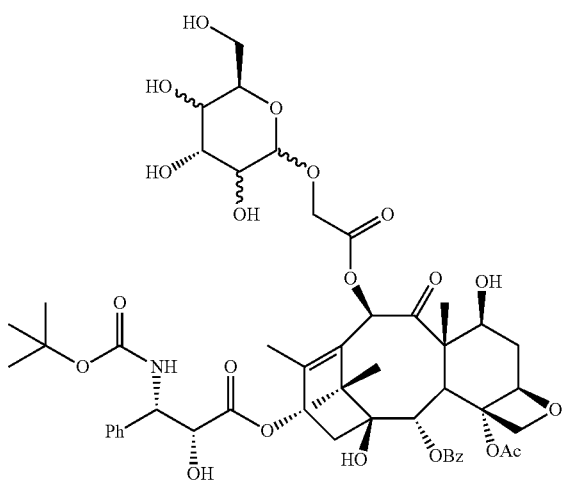

wherein the α-glucosyl group may be a β-glucosyl group, α-galactosyl group, β-galactosyl group, or α-mannosyl group.

(4)

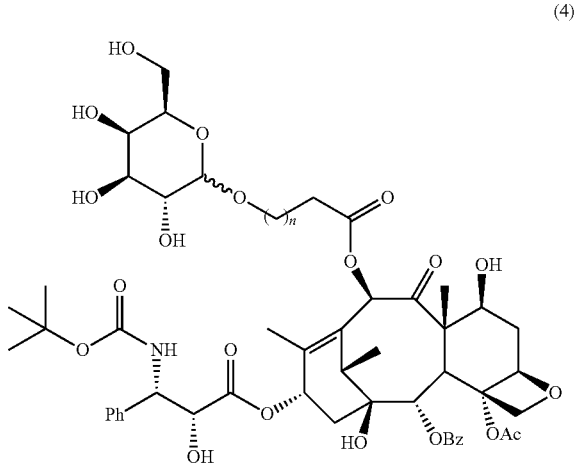

wherein n is 2, 3, 4, 6, or 8.

The docetaxel monoglycoside can be produced using a known method. For example, the docetaxel monoglycoside can be produced by suitably referring to the method described in, for example, Heterocycles, 2001, Vol. 54, No. 2, 561-566. Biol. Pharm. Bull. 2008, and 31(6), 1155-1158 (2008).

The type of liposome produced by the first embodiment production method of the present invention is determined according to the liposome constituent lipids; however, the liposome may be any of anionic liposome, cationic liposome, and amphoteric liposome. For example, cationic liposomes are preferable compared to other liposomes from the viewpoint of efficient material introduction to cells; however, since cationic liposomes cause non-specific adsorption to cells, they exhibit a poor DDS effect, i.e., a poor effect of delivering the liposome encapsulating a paclitaxel monoglycoside and/or a docetaxel monoglycoside obtained by the method of the present invention to specific cells. Accordingly, cationic liposomes are not preferable.

The liposome formation treatment method in the first embodiment production method of the present invention is a known method, and not particularly limited. Examples include a thin-film hydration method, freeze-dry method, droplet method, AC-electric field-dependent electroformation, ultrasonic method, reverse-phase evaporation method, bubbling method, spray-dry method, method using a $CO_2$/$H_2O$ emulsion, method using a microchannel, etc.

The liposome formation treatment in the first embodiment production method of the present invention is specifically explained. For example, the phospholipid, cholesterol, etc., mentioned above are dissolved in a suitable organic solvent, and the resultant is placed in a suitable container to distil off the solvent under reduced pressure, thereby forming a phospholipid film in the container. The solution containing a paclitaxel monoglycoside and/or a docetaxel monoglycoside, and preferably a buffer therefor are added to the phospholipid film, followed by stirring, thus obtaining a liposome encapsulating a paclitaxel monoglycoside and/or a docetaxel monoglycoside. The thus-obtained liposome may be subjected to lyophilization, and then stored.

The particle size of the liposome obtained by the first embodiment production method of the present invention is not particularly limited; however, it is generally about 50 to 300 nm to preferably use the liposome as a liposome formulation encapsulating a paclitaxel monoglycoside and/or a docetaxel monoglycoside having an anti-cancer effect. A liposome formulation satisfying the above numerical range is preferable because it can pass through a microvessel, etc., particularly a microvessel generated by angiogenesis induced by cancer cells. A liposome with a particle size of 50 nm or more is preferable because substantial leakage to cells is not likely to occur. Further, a liposome with a particle size of 300 nm or less is preferable because it is not likely to undergo phagocytosis by leucocytes (macrophages) in blood after being administered to a living body.

In view of the above, the particle size of the liposome obtained by the first embodiment production method of the present invention can be adjusted to a predetermined particle size. Specifically, the size of the liposome can be adjusted by changing various conditions in the liposome formation treatment beforehand. The size can also be adjusted by making the liposome pass through a filter whose pore diameter is adjusted. As the method for making a liposome formulation pass through a filter to thereby adjust the particle size of the liposome formulation, a method using an extruder, etc., can be listed.

The liposome obtained by the first embodiment production method of the present invention may have an antibody recognizing a cancer cell. The antibody may be a monoclonal antibody or a polyclonal antibody; and the kind of animals from which antibodies are derived is not particularly limited.

Antibodies having any molecular structure can be used as long as molecules have antigen recognition ability. Examples include single-chain antibodies, domino antibodies, scFvs, polyvalent antibodies, bispecific antibodies, Fab antibodies, F(ab')$_2$ antibodies, chimeric antibodies, humanized antibodies, etc. Antibodies are not limited to those having an immunoglobulin structure, as typified by IgG.

The antibody is bound to the lipid bilayer membrane of the liposome obtained by the production method of the present invention, and the binding mode is not particularly limited. By suitably selecting the binding mode depending on the structure of the antibody used, a liposome having an intended antibody can be obtained.

For example, when the antibody is immunoglobulin, SPDP (N-succinimidyl 3-(2-pyridyldithio)-propionate), etc., may be used to bind the antibody to the liposome.

To carry the antibody, the antibody may be bound to the liposome encapsulating a paclitaxel monoglycoside and/or a docetaxel monoglycoside according to the first embodiment production method of the present invention, or the antibody may be bound to liposome constituent lipids beforehand. To present a larger portion of the antibody to be bound on the surface of the liposome, it is preferable to bind the antibody to the liposome encapsulating a paclitaxel monoglycoside and/or a docetaxel monoglycoside according to the production method of the present invention.

The antibody of the liposome of the present invention recognizes cancer cells. Although the cancer cell is not particularly limited, examples include lung cancer cells, non-small cell lung cancer cells, breast cancer cells, esophageal cancer cells, gastric cancer cell, liver cancer cells, pancreatic cancer cells, colon cancer cells, ovarian cancer cells, cervical cancer cells, endometrial cancer cells, prostate cancer cells, head and neck cancer cells (oral cancer cells), pharyngeal cancer cells, laryngeal cancer cells, nasal or nasal sinus cancer cells, salivary gland cancer cells, thyroid cancer cells, etc.

Of these, based on the clinical application knowledge of paclitaxel, non-small cell lung cancer cells, breast cancer cells, esophageal cancer cells, gastric cancer cells, endometrial cancer cells, ovarian cancer cells, prostate cancer cells, etc., are preferable.

The antibody recognizing a cancer cell is an antibody specifically recognizing biomolecules such as proteins (e.g., CD proteins forming CD protein groups such as CD44 and CD13, receptors for growth factors or hormones, and proteins having a transmembrane domain or membrane-binding domain), peptides, sugar chains, etc., present on the surface layer of the cancer cell. The antibody is not particularly limited, and may be an antibody that is known to be expressed on the surface layer of each cancer cell.

Examples of the antibody recognizing a breast cancer cell include antibodies recognizing biomolecules such as proteins, peptides, sugar chains, etc., present on the surfaces of breast cancer cells extracted from breast cancer patients, and cells derived from breast cancer tissues, such as Hs274.T cell, Hs280.T cell, Hs281.T cell, Hs343.T cell, Hs362.T cell, Hs739.T cell, Hs741.T cell, Hs742.T cell, Hs190.T cell, Hs319.T cell, Hs329.T cell, Hs344.T cell, Hs350.T cell, Hs371.T cell, Hs748.T cell, Hs841.T cell, Hs849.T cell, Hs851.T cell, Hs861.T cell, Hs905.T cell, Hs479.T cell, Hs540.T cell, Hs566(B).T cell, Hs605.T cell, Hs606 cell, BT-20 cell, UACC-812 cell, HCC1954 cell, Hs574.T cell, BT-483 cell, BT-549 cell, DU4475 cell, Hs578T cell, BT-474 cell, UACC-893 cell, HCC38 cell, HC C70 cell, HCC202 cell, HCC1143 cell, HCC1187 cell, HCC1395 cell, HCC1419 cell, HCC1500 cell, HCC1599 cell, HCC1937 cell, HCC2157 cell, HCC2218 cell, HCC1569 cell, MB157 cell, SK-BR3 cell, MDA-MB-330 cell, MDA-MB-453 cell, MDA-MB-157 cell, MDA-MB-134 cell, T-47D cell, ZR-75 cell, and MCF-7 cell. Specifically, anti-HER2 antibody (anti-ErbB2 antibody), anti-CEA antibody, etc., can be listed.

Examples of the antibody recognizing a lung cancer cell include antibodies recognizing biomolecules such as proteins, peptides, sugar chains, etc. present on the surfaces of lung cancer cells extracted from lung cancer patients, and cells derived from lung cancer tissues, such as Hs229.T cell, NCI-H2066 cell, NCI-H2286 cell, NCI-H1703 cell, Hs573.T cell, A549 cell, A427 cell, N417 cell, NCI-H596 cell, SW1573 cell, NCI-H835U cell, MC11 cell, NCI-H727 cell, NCI-H720 cell, NCI-H810 cell, NCI-H292 cell, NCI-H2126 cell, H69 cell, NCI-H1688 cell, NCI-H1417 cell, NCI-H1672 cell, NCI-H1836 cell, DMS79 cell, DMS53 cell, DMS114 cell, SW1271 cell, NCI-H2227 cell, NCI-H1963 cell, SHP-77 cell, H69 cell, H69AR cell, NCI-H2170 cell, NCI-H520 cell, and SW900 cell. Specifically, anti-HER2 antibody, anti-EGFR antibody, anti-CEA antibody, etc., can be listed.

Examples of the antibody recognizing a non-small cell lung cancer cell include antibodies recognizing biomolecules such as proteins, peptides, sugar chains, etc., present on the surfaces of non-small cell lung cancer cells extracted from non-small cell lung cancer patients, and cells derived from an antibody recognizing non-small cell lung cancer tissues, such as NCI-H23 cell, NCI-H522 cell, NCI-H1435 cell, NCI-H1563 cell, NCI-H1651 cell, NCI-H1734 cell, NCI-H1793 cell, NCI-H1838 cell, NCI-H1975 cell, NCI-H2073 cell, NCI-H2085 cell, NCI-H2228 cell, NCI-H2342 cell, NCI-H2347 cell, NCI-H2135 cell, NCI-H2172 cell, and NCI-H2444 cell. Specifically, anti-HER2 antibody, anti-EGFR antibody, etc., can be listed.

Examples of the antibody recognizing an esophageal cancer cell include antibodies recognizing biomolecules such as proteins, peptides, sugar chains, etc., present on the surfaces of esophageal cancer cells extracted from esophageal cancer patients, and cells derived from esophageal cancer tissues, such as SGF-3 cell, EC-YO cell, TE-1 cell, TE-2 cell, TE-3 cell, TE-4 cell, TE-5 cell, TE-6 cell, TE-7 cell, TE-8 cell, TE-9 cell, TE-10 cell, TE-11 cell, TE-12 cell, TE-13 cell, TE-14 cell, and TE-15 cell. Specifically, anti-HER2 antibody, anti-EGFR antibody, etc., can be listed.

Examples of the antibody recognizing a gastric cancer cell include antibodies recognizing biomolecules such as proteins, peptides, sugar chains, etc., present on the surfaces of gastric cancer cells extracted from gastric cancer patients, and cells derived from gastric cancer tissues, such as AZ521 cell, AGS cell, SNU-1 cell, SNU-5 cell, SNU-16 cell, NCI-N87 cell, Hs746T cell, and KATO III cell. Specifically, anti-HER2 antibody, anti-EGFR antibody, anti-CEA antibody, anti-SLX antibody, etc., can be listed.

Examples of the antibody recognizing a liver cancer cell include antibodies recognizing biomolecules such as proteins, peptides, sugar chains, etc. on the surfaces of liver cancer cells extracted from liver cancer patients, and cells derived from liver cancer tissues, such as HepG2 cell, Huh-7 cell, C3A cell, SNU-398 cell, SNU-449 cell, SNU-182 cell, SNU-475 cell, Hep3B2.1-7 cell, PLHC-1 cell, SNU-387 cell, SNU-423 cell, and SK-HEP-1 cell. Specifically, anti-HER2 antibody, etc., can be listed.

Examples of the antibody recognizing a pancreatic cancer cell include antibodies recognizing biomolecules such as proteins, peptides, sugar chains, etc., present on the surfaces of pancreatic cancer cells extracted from pancreatic cancer patients, and cells derived from pancreatic cancer tissues, such as MIAPaCa-2 cell, BxPC-3 cell, HPAF-II cell, HPAC cell, Panc03.27 cell, Panc08.13 cell, Panc02.03 cell, Panc02.13 cell, Panc04.03 cell, Panc05.04 cell, Capan-2 cell, CFPAC-1 cell, PL45 cell, Panc10.05 cell, PANC-1 cell, AsPC-1 cell, Capan-1 cell, SW1990 cell, Hs766T cell, and SU.86.86 cell. Specifically, anti-HER 2 antibody, anti-CEA antibody, anti-SLX antibody, etc., can be listed.

Examples of the antibody recognizing a colon cancer cell include antibodies recognizing biomolecules such as proteins, peptides, sugar chains, etc., present on the surfaces of colon cancer cells extracted from colon cancer patients, and cells derived from colon cancer tissues, such as WiDr cell, Caco-2 cell, NCI-H548 cell, Hs255.T cell, TAC-1 cell, COLO320DM cell, COLO320HSR cell, DLD-1 cell, HCT-15 cell, SW480 cell, SW403 cell, SW48 cell, SW1116 cell, SW948 cell, SW1417 cell, LS123 cell, LS180 cell, LS174T cell, C2BBe1 cell, Hs257.T cell, Hs587.Int cell, HT-29 cell, HCT-8 cell, Hs675.T cell, HCT116 cell, ATRFLOX cell, Hs698.T cell, SW626 cell, SNU-C1 cell, COLO205 cell, COLO201 cell, SW620 cell, LoVo cell, SK-CO-1 cell, and T84 cell. Specifically, anti-HER2 antibody, anti-EGFR antibody, anti-CEA antibody, etc., can be listed.

Examples of the antibody recognizing an ovarian cancer cell include antibodies recognizing biomolecules such as proteins, peptides, sugar chains, etc., present on the surfaces of ovarian cancer cells extracted from ovarian cancer patients, and cells derived from ovarian cancer tissues, such as PA-1 cell, Caov-3 cell, TOV-21G cell, TOV-112D cell, Hs38.T cell, Hs571.T cell, ES-2 cell, TE84.T cell, NIH:OVCAR-3 cell, SK-OV-3 cell, Caov-4 cell, and OV-90 cell. Specifically, anti-HER2 antibody can be listed.

Examples of the antibody recognizing a cervical cancer cell include antibodies recognizing biomolecules such as proteins, peptides, sugar chains, etc., present on the surfaces of cervical cancer cells extracted from cervical cancer patients, and cells derived from cervical cancer tissues, such as HeLa cell, HeLa229 cell, HeLaS3 cell, H1HeLa cell, Hs588.T cell, GH329 cell, GH354 cell, HeLaNR1 cell, C-4I cell, C-4II cell, DoTc2 4510 cell, C-33A cell, SW756 cell, SiHa cell, HT-3 cell, MS75 cell, CaSki cell, and ME-180 cell. Specifically, anti-HER2 antibody, etc., can be listed.

Examples of the antibody recognizing an endometrial cancer cell include antibodies recognizing biomolecules such as proteins, peptides, sugar chains, etc., present on the surfaces of endometrial cancer cells extracted from endometrial cancer patients, and cells derived from endometrial cancer tissues, such as HHUA cell, KLE cell, HEC-1-A cell, HEC-1-B cell, HEC-6 cell, HEC-50 cell, HEC-59 cell, HEC-108 cell, HEC-116 cell, RL95-2 cell, SK-UT-1 cell, SK-UT-1B cell, MES-SA cell, MES-SA/Dx5 cell, MES-SA/M2 cell, AN3CA cell, SNG-P cell, and SNG-M cell. Specifically, anti-HER2 antibody, anti-CEA antibody, etc., can be listed.

Examples of the antibody recognizing a prostate cancer cell include antibodies recognizing biomolecules such as proteins, peptides, sugar chains, etc., present on the surfaces of prostate cancer cells extracted from prostate cancer patients, and cells derived from prostate cancer tissues, such as LNCaP cell, 22Rv1 cell, PC-3 cell, MDA PCa 2b cell, TRAMP-C3 cell, DU145 cell, NCI-H660 cell, TSU-PR1PC-82 cell, PPC-1 cell, and VCRU-Pr-2 cell. Specifically, anti-HER2 antibody, anti-EGFR antibody, etc., can be listed.

Examples of the antibody recognizing an oral cancer cell from among head and neck cancer cells include antibodies recognizing biomolecules such as proteins, peptides, sugar chains, etc., present on the surfaces of oral cancer cells extracted from oral cancer patients, and cells derived from oral cancer tissues, such as Hs53.T cell.

Examples of the antibody recognizing a pharyngeal cancer cell from among head and neck cancer cells include antibodies recognizing biomolecules such as proteins, peptides, sugar chains, etc., present on the surfaces of pharyngeal cancer cells extracted from pharyngeal cancer patients, and cells derived from pharyngeal cancer tissues, such as C666-1 cell, NPC-TY861 cell, MPC-Y851 cell, MPC-K852 cell, KKK-YT cell, and MPC-ST cell.

Examples of the antibody recognizing a laryngeal cancer cell from among head and neck cancer cells include antibodies recognizing biomolecules such as proteins, peptides, sugar chains, etc., present on the surfaces of laryngeal cancer cells extracted from laryngeal cancer patients, and cells derived from laryngeal cancer tissues, such as FaDu cell, Hs840.T cell, and Detroit 562 cell.

Examples of the antibody recognizing a nasal or nasal sinus cancer cell from among head and neck cancer cells include antibodies recognizing biomolecules such as proteins, peptides, sugar chains, etc., present on the surfaces of nasal or nasal sinus cancer cells extracted from nasal or nasal sinus cancer patients, and cells derived from nasal or nasal sinus cancer tissues, such as RPMI2650 cell.

Examples of the antibody recognizing a salivary gland cancer cell from among head and neck cancer cells include antibodies recognizing biomolecules such as proteins, peptides, sugar chains, etc., present on the surfaces of salivary gland cancer cells extracted from salivary gland cancer patients, and cells derived from salivary gland cancer tissues, such as SGT-1 cell.

Examples of the antibody recognizing a thyroid cancer cell from among head and neck cancer cells include antibodies recognizing biomolecules such as proteins, peptides, sugar chains, etc., present on the surfaces of thyroid cancer cells extracted from thyroid cancer patients, and cells derived from thyroid cancer tissues, such as HTC/C3 cell, SW579 cell, and TT cell.

Specifically, anti-HER2 antibody, anti-EGFR antibody, etc., can be listed as antibodies recognizing head and neck cancer cells.

The most preferable antibody is anti-HER2 antibody because an extremely large amount of anti-HER2 antibody is expressed on the surface layer of the cancer cell to which the paclitaxel monoglycoside and/or docetaxel monoglycoside of the liposome formulation of the present invention is applied.

The antibody can be produced using known methods, and effective ingredients obtained from antibody drugs, which are typically molecular targeting drugs, can be used. For example, an anti-HER2 antibody for HER2 specifically recognizing the breast cancer cells is an effective ingredient of the antibody drug that is commercially available as Herceptin® from Chugai Pharmaceutical Co., Ltd.

Another embodiment (sometimes referred to as the "second embodiment production method") of the method for producing a liposome of the present invention is a method for producing a liposome encapsulating a paclitaxel monoglycoside and/or a docetaxel monoglycoside, and having an antibody specifically recognizing a cancer cell, the method comprising the step of bringing the liposome encapsulating a polyoxyethylene ester derivative, lower alcohol, and buffer or water into contact with a solution in which a paclitaxel monoglycoside and/or docetaxel monoglycoside is dissolved in an alkylene glycol-containing buffer or water.

The second embodiment production method may include the step of bringing a liposome encapsulating a polyoxyethylene ester derivative, lower alcohol, and buffer or water into contact with a solution in which a paclitaxel monoglycoside and/or a docetaxel monoglycoside is dissolved in an alkylene glycol-containing buffer or water, and then the step of binding an antibody specifically recognizing a cancer cell to the obtained liposome (method 1); or the step of bringing a liposome obtained by binding an antibody specifically recognizing a cancer cell to a liposome encapsulating a polyoxyethylene ester derivative, lower alcohol, and buffer or water, to a solution in which a paclitaxel monoglycoside and/or a docetaxel monoglycoside is dissolved in an alkylene glycol-containing buffer or water (method 2).

As the "paclitaxel monoglycoside," "docetaxel monoglycoside," "cancer cell," "antibody specifically recognizing a cancer cell", "liposome" lipid composition, "liposome" production method (formation treatment method), "liposome" particle size, method of binding an antibody specifically recognizing a cancer cell to the "liposome," "polyoxyethylene ester derivative," "lower alcohol," etc., in the second embodiment production method, those detailed in the first embodiment production method of the present invention can be used unmodified, or with suitable modification. The liposome may be in the state before or after binding of an antibody specifically recognizing a cancer cell, and before and after encapsulating a paclitaxel monoglycoside and/or a docetaxel monoglycoside.

Regarding the lipid composition of the liposome in the second embodiment production method, DPPC and cholesterol are preferably included. The specific material quantity ratio of DPPC and cholesterol is not particularly limited, and is generally about 3:0.5 to 3, preferably 3:1 to 3, more preferably 3:1 to 2, and even more preferably 3:1.

Regarding the polyoxyethylene ester derivative, lower alcohol, and buffer or water encapsulated in the liposome in the second embodiment production method, the volume ratios thereof are not particularly limited as in the first embodiment production method. The polyoxyethylene ester derivative may be generally contained in an amount of 0.1 to 0.2, preferably 0.12 to 0.19, and more preferably 0.13 to 0.18 part by volume per part by volume of buffer or water.

The lower alcohol is generally contained in an amount of 0.1 to 0.2, preferably 0.12 to 0.19, and more preferably 0.13 to 0.18 part by volume per part by volume of buffer or water.

Regarding the method for encapsulating a polyoxyethylene ester derivative, lower alcohol, and buffer or water in the liposome, the first embodiment production method described above can be suitably referenced.

Although the alkylene glycol in the second embodiment production method is not particularly limited, examples include ethylene glycol, propylene glycol, butylene glycol, etc. These alkylene glycols may be suitably used in combination.

The amount of alkylene glycol used is generally about 0.1 to 1.5, preferably about 0.2 to 1.0, more preferably about 0.3 to 0.8, and most preferably 0.4 to 0.7 part by volume per part by volume of buffer or water.

The solubility of paclitaxel monoglycoside and/or docetaxel monoglycoside in an alkylene glycol-containing buffer or water is generally about 0.1 to 2 mg/mL.

In the second embodiment production method, the time in which a liposome encapsulating a polyoxyethylene ester derivative, lower alcohol, and buffer or water is brought into contact with a solution in which a paclitaxel monoglycoside and/or a docetaxel monoglycoside is dissolved in an alkylene glycol-containing buffer or water is not particularly limited, and is generally about 5 to 60, preferably about 10 to 30, and more preferably about 10 to 20 minutes.

The temperature and other conditions for contacting are not particularly limited, and are determined according to a known remote loading method.

In the second embodiment production method of the present invention, the introduction efficiency of paclitaxel monoglycoside and/or docetaxel monoglycoside into the liposome is generally about 50 to 90%, more preferably about 70 to 90%. The introduction efficiency can be determined based on the encapsulation efficiency (EE:%) explained in the Examples below.

In both the first embodiment and the second embodiment, the method for producing a liposome of the present invention may include the step of purifying the obtained liposome. The specific purification method is not particularly limited, and a known method can be used. For example, a chromatographic method, ultrafiltration method, and dialysis method, each using a gel filtration resin, etc., can be listed.

The liposome obtained by the method above can be suitably stored according to a known method, and is not particularly limited. The liposome may be, for example, subjected to lyophilization, or stored in a liquid of p-hydroxybenzoate, phenoxyethanol, etc., optionally containing a known preservative.

The liposome obtained by the production method of the present invention can provide an efficient anti-cancer activity effect on the cancer cells by the paclitaxel monoglycoside and/or docetaxel monoglycoside contained in the liposome. Specifically, the growth of the cancer cells can be inhibited, and moreover the cancer cells can be minimized. The liposome obtained by the production method of the present invention, which encapsulates a paclitaxel monoglycoside and/or docetaxel monoglycoside, or encapsulates a solution liquid of paclitaxel monoglycoside and/or docetaxel monoglycoside, is specifically delivered to a cancer cell by the effect of the antibody contained in the liposome. Therefore, such a liposome has an advantage of reduced side effects.

Accordingly, the liposome having an antibody specifically recognizing a cancer cell, which is obtained by the production method of the present invention, is useful as a cancer-treating agent when used as a liposome formulation.

Liposome Formulation

The liposome formulation of the present invention encapsulates a solution liquid of paclitaxel monoglycoside and/or docetaxel monoglycoside, and has an antibody specifically recognizing a cancer cell.

The liposome formulation of the present invention may be produced using the liposome unmodified, which is obtained by the production method of the present invention, or by using a known formulation technique.

Specifically, the liposome formulation of the present invention encapsulates a solution liquid of paclitaxel monoglycoside and/or docetaxel monoglycoside, and has an antibody specifically recognizing a cancer cell.

The solution liquid of paclitaxel monoglycoside and/or docetaxel monoglycoside in the liposome formulation of the present invention is preferably such that a paclitaxel monoglycoside and/or a docetaxel monoglycoside is dissolved in a mixed solvent containing a polyoxyethylene ester derivative, lower alcohol, and buffer or water.

As the "paclitaxel monoglycoside," "docetaxel monoglycoside," "cancer cell," "antibody specifically recognizing a cancer cell, "liposome" lipid composition, "liposome" production method (formation treatment method), "liposome" particle size, "method of binding an antibody specifically recognizing a cancer cell to the "liposome," "polyoxyethylene ester derivative," "lower alcohol," etc., in the liposome formulation of the present invention, those detailed in the method for producing a liposome of the present invention in the above embodiments can be used unmodified, or with suitable modification.

The lipid composition of the liposome is the same as that of the method for producing a liposome of the present invention, and DPPC and cholesterol are generally contained in a material quantity ratio of about 3:0.5 to 3, preferably 3:1 to 3, more preferably 3:1 to 2, and most preferably 3:1.

The mol of the paclitaxel monoglycoside and/or docetaxel monoglycoside in the liposome formulation of the present invention is generally about 1.0 to $15.0 \times 10^{-2}$, and preferably 7.0 to $15.0 \times 10^{-2}$ per mol of the total lipids of the liposome. The mol of the paclitaxel monoglycoside and/or docetaxel monoglycoside can be determined using loading efficiency (LE:%) explained in the Examples below.

The liposome formulation of the present invention is efficiently and specifically delivered to a cancer cell when administered to a living body. The liposome formulation also has an invasion effect into the cell after delivery. The administration method of the liposome formulation is not particularly limited; however, it is preferably directly administered to blood. Specific examples of the administration include intravenous administration, intraarterial administration, intramuscular administration, intracardiac administration, subcutaneous administration, intraosseous administration, intradermal administration, intrathecal administration, intraperitoneal administration, intravesical administration, etc. The means of administration is not particularly limited, and known methods such as administration, infusion, and perfusion pump can be used.

The administration amount of the liposome formulation of the present invention is determined according to the age, sex, severity of cancer, etc., of a patient who desires cancer treatment, and is not specifically limited. The administration amount may be about 10 to 100 mg/kg per each administration in view of the amount of paclitaxel monoglycoside and/or docetaxel monoglycoside in the liposome formulation. The administration interval, number of administrations, etc., are suitably determined depending on the age, sex, severity of cancer, etc., of a patient who desires cancer treatment. The cancer to be treated by administration is not particularly limited as long as it is a cancer described in the production method of the liposome of the present invention, and can be suitably selected.

When the liposome formulation having an antibody of the present invention is administered to a living body as a DDS, if the liposome formulation problematically accumulates not only on the target site, but also on the liver to a certain degree, modifying the liposome by, for example, a polyethylene glycol may be effective. A known method can be suitably used for modification.

EXAMPLES

The present invention is detailed below. However, the present invention is not limited to the Examples shown below.

Test Example 1: Solubility of 7-α-Glucosyloxyacetylpaclitaxel

The solubility of 7-α-glucosyloxyacetylpaclitaxel (hereinbelow referred to as gPTX in the Examples) represented by chemical formula (1) below was examined.

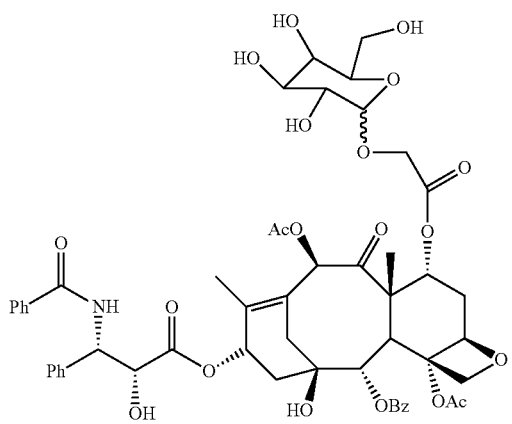

(1)

Powdery gPTX and paclitaxel (hereinbelow, referred to as PTX in the Examples) produced by the method disclosed in NPL 1 were individually weighed in predetermined amounts, followed by addition of ethanol (120 μL) and mixing using a vortex. Cremophor® EL (available from Wako Pure Chemical Industries. Ltd.) (120 μL) was further mixed with each solution liquid, and then PBS (pH 7.4, 760 μL) was mixed. The solubility of each of the gPTX and PTX was confirmed. Table 1 shows the results.

TABLE 1

| Concentration (mg/ml) | PTX | gPTX |
|---|---|---|
| 2 | o | o |
| 3 | x | — |
| 10 | x | o |
| 20 | x | o |
| 30 | — | x |

* In the table, x, o, and — respectively indicate insoluble, soluble, and not performed.

The results revealed that the PTX, which is an aglycone, was dissolved only at a concentration of about 2 mg/ml, whereas the gPTX was dissolved at a high concentration, i.e., 20 mg/ml. Specifically, it was revealed that although PTX and gPTX are both generally not likely to dissolve in water, and PTX did not show a sufficient solubility even in a mixed nonaqueous solvent containing Cremophor:ethanol:PBS (pH 7.4) in a volume ratio of 12:12:76, gPTX dissolved in the mixed nonaqueous solvent at an extremely high concentration.

Table 2 shows the results in which the solubility of gPTX in a 10 mM phosphate buffer containing 10 to 40% (volume) ethylene glycol (EG) was similarly examined as comparative examples. In all cases, gPTX was mixed so that the concentration became 1 mg/mL.

TABLE 2

| | Ethylene glycol (EG) % | | | |
|---|---|---|---|---|
| | 10 | 20 | 30 | 40 |
| Solubility of 1 mg/mL gPTX | x | x | Δ | o |

* In the table, x, Δ, and o respectively indicate insoluble, partially soluble, and soluble.

The results revealed that the gPTX was not dissolved in the PBS containing 10 to 20% (volume) ethylene glycol, was partially dissolved in the PBS containing 30% (volume) ethylene glycol, and was dissolved in the PBS containing 40% (volume) ethylene glycol. The solubility of gPTX herein was approximately about 1 mg/mL. Accordingly, it was revealed that the gPTX itself was hardly dissolved in the aqueous solvent alone, but dissolved in the mixed solvent containing 30 to 40% (volume) ethylene glycol.

Test Example 2: Liposome Encapsulating 7-α-Glucosyloxyacetylpaclitaxel 1,2-Dipalmitoyl-rac-glycero-3-phosphocholine (DPPC), 1,2-dipalmitoyl-sn-glycerol-3-phospho-rac-(1-glycerol) sodium salt (DPPG), and cholesterol were respectively weighed in amounts of 13.5, 1.5, and 1.5 mg, and mixed in a 50 ml eggplant flask. The mixed lipid was dissolved in an organic solvent (3 ml) (chloroform:methanol=9:1), then dried using a rotary evaporator, and then vacuum-dried for 2 hours to completely remove the solvent, thus preparing a lipid film.

Subsequently, after the eggplant flask was immersed in a hot bath at 60° C. for five minutes, a gPTX solution (1 ml) (Cremophor:ethanol:ultra-pure water=12:12:76, volume ratio) adjusted to a concentration of 20 mg/ml, or a PTX solution (Cremophor:ethanol:ultra-pure water=12:12:76, volume ratio) at a concentration of 2 mg/ml was added thereto to dissolve the lipid film, thus preparing a multilamellar vesicle (MLV).

The MLV was subjected to five-minute sonication three times with intervals of one minute to thereby prepare a small lamellar vesicle (SLV). To remove an unencapsulated drug solution and free lipid, ultrafiltration (Amicon Ultra 100K membrane (Millipore)) was performed. Hereinbelow, a liposome encapsulating gPTX was referred to as gPTX-L, and a liposome encapsulating PTX was referred to as PTX-L.

In a comparative example, the above-mentioned 1 mg/ml gPTX solution (10 mM phosphate buffer containing 40% (volume) ethylene glycol) was used in place of the 20 mg of gPTX solution to encapsulate gPTX in a liposome.

Subsequently, an experiment for encapsulating the gPTX in a liposome having an antibody was performed. DPPC, DPPG, and cholesterol were respectively weighed in amounts of 13.5, 1.5, and 1.5 mg, and mixed in a 50 ml eggplant flask. After the mixed lipid was dissolved in an organic solvent (3 ml) (chloroform:methanol=9:1), 27 µl (0.2 mg) of 8 mM N-3-(2-dithiopyridyl)propionyldipalmitoylphosphatidyl ethanolamine (DTP-DPPE) solution was added thereto. Thereafter, the mixture was dried using a rotary evaporator, and then vacuum-dried for 2 hours to completely remove the solvent, thus preparing a lipid film.

Subsequently, after the eggplant flask was immersed in a hot bath at 60° C. for five minutes, a gPTX solution (1 ml) (Cremophor:ethanol:ultra-pure water=12:12:76, volume ratio) adjusted to a concentration of 20 mg/ml was added thereto to dissolve the lipid film, thus preparing a multilamellar vesicle (MLV).

The MLV was subjected to five-minute sonication three times with intervals of one minute to thereby prepare a small lamellar vesicle (SLV). To remove an unencapsulated drug solution and free lipid, ultrafiltration (Amicon Ultra 100K membrane (Millipore)) was performed.

At the same time, an antibody to be bound to the liposome was prepared. N-succinimidyl 3-(2-pyridyldithio) propionate (SPDP) (1 mg) was dissolved in 500 µl of dehydrated methanol to obtain a 2 mg/ml SPDP solution. The SPDP solution (5 µl) was placed in a 1 mg/ml trastuzumab (humanized anti-HER2 monoclonal antibody) solution (1 ml), followed by stirring for 30 minutes at room temperature. To remove non-binding SPDP, a SPDP modified trastuzumab solution was placed in a dialysis tube (molecular weight cutoff: 14,000), and dialyzed using a 100 mM acetate buffer (pH 4.5). The dialysis was performed in the dark at 4° C., and the external buffer was changed four times at three-hour intervals, and two times with 12-hour intervals.

A 50 mM dithiothreitol (DTT) solution (500 ill) was mixed with the SPDP-modified trastuzumab solution, and the mixture was stirred at room temperature for 30 minutes. To remove unreacted DTT, and a byproduct of methylpyridine-2-thione, ultrafiltration (Amicon Ultra 10K membrane (Millipore)) was performed.

After the filtration, the resultant was mixed with the liposome encapsulating PTX or gPTX to bind the trastuzumab to the liposome.

Hereinbelow, a liposome in which the gPTX or PTX is encapsulated in a liposome having an antibody is respectively referred to as gPTX-IL or PTX-IL, and a liposome in which the gPTX or PTX is encapsulated in a liposome having no antibody is respectively referred to as gPTX-L or PTX-L.

In a comparative example, an experiment was performed in which the above-mentioned 1 mg/ml gPTX solution (10 mM phosphate buffer containing 40% (volume) ethylene glycol) was used in place of the gPTX solution to encapsulate gPTX in a liposome having an antibody.

The efficiency of paclitaxel monoglycoside encapsulated in the obtained liposome or immunoliposome was calculated as follows. First, the standard curve of each of the gPTX and PTX was obtained. The standard curve was made by detecting 0.01 to 0.5 mg/ml drug solutions (Cremophor:ethanol: PBS (pH 7.4) 12:12:76, volume ratio) using HPLC, and based on the peak areas obtained at respective drug concentrations.

Next, 0.1% Triton X-100 (1/10 volume) was added to a prepared liposome, and the liposome was broken by sonication. Thereafter, the solution (10 µl) was measured by HPLC, and the encapsulated drug amount was obtained using the standard curve. As an HPLC column, WP300 C18 (5 µm, 4.6×150 mm) was used. Measurement conditions were such that the detection wavelength was 227 nm, a solvent of methanol:ultra-pure water=6:4 was used in moving phase, and the fluid was delivered at a flow rate of 1.0 ml/min.

Using the following formulae (1) and (2), the encapsulation efficiency (EE) and loading efficiency (LE) were calculated based on the obtained drug amount.

$$\text{Encapsulation efficiency (EE:\%)}=\text{drug amount/amount of drug initially used} \times 100 \quad (1)$$

$$\text{Loading efficiency (LE:\%)}=\{(\text{drug amount/drug mol weight})/\text{initial lipid mol number}\} \times 100 \quad (2)$$

The particle size of the obtained liposome was measured as a Z-average particle size based on the dynamic light scattering method. Table 3 shows the results.

TABLE 3

| Drug used | Concentration solvent | Particle size (nm) | EE | LE |
|---|---|---|---|---|
| PTX-L | Containing Cremophor (2 mg/mL) | 210.0 ± 67.5 | 12.1 | 1.2 |

TABLE 3-continued

| Drug used | Concentration solvent | Particle size (nm) | EE | LE |
|---|---|---|---|---|
| gPTX-L | Containing | 157.0 ± 40.8 | 17.6 | 13.7 |
| gPTX-IL | Cremophor (20 mg/mL) | 205.5 ± 37.8 | 14.8 | 11.4 |
| PTX-L | 40% EG | N.D. | N.D. | N.D. |
| gPTX-L | (1 mg/mL) | N.D. | 0.41 | $3.18 \times 10^{-2}$ |
| gPTX-IL |  | N.D. | 0.51 | $3.93 \times 10^{-2}$ |

The results shown in Table 3 revealed that the PTX dissolved in 40% ethylene glycol was not encapsulated in the liposome. Further, it was revealed that the encapsulation efficiency of the gPTX dissolved in the solvent containing Cremophor, etc., was higher than that of the PTX.

Regarding the loading efficiency of PTX to the liposome constituent lipids, the PTX dissolved in the Cremophor-containing solvent showed a loading efficiency of only about 1.2%, whereas the gPTX dissolved in the Cremophor-containing solvent showed a loading efficiency of 13.7%; and the gPTX in the encapsulation experiment in the liposome having an antibody showed a loading efficiency of 11.4%. This indicated that the loading amount of gPTX per liposome constituent lipids was about 9.5 to 11.4 times higher than that of PTX. This revealed that gPTX had an advantage of being encapsulated in the liposome.

Regarding the encapsulation efficiency, only about 0.41% of the gPTX dissolved in the 40% (volume) ethylene glycol solution was encapsulated in the liposome, and only about 0.51% of the gPTX dissolved in the 40% (volume) ethylene glycol solution was encapsulated in the liposome having an antibody whereas 17.6% of the gPTX dissolved in the Cremophor-containing solvent was encapsulated in the liposome, and 14.8 of the gPTX dissolved in the Cremophor-containing solvent was encapsulated in the liposome having an antibody, indicating that the encapsulation efficiency was increased by about 30 to 40 times.

Thus, the results indicated that to encapsulate gPTX in a liposome, the use of gPTX dissolved in the Cremophor-containing solvent was greatly advantageous.

Test Example 3: Anti-Cancer Activity Evaluation $IC_{50}$ of each of the PTX and gPTX dissolved in DMSO, and gPTX-L and gPTX-IL prepared by using gPTX dissolved in a 40% (volume) ethylene glycol solution was measured by an MTT assay. As a test target cell, SK-BR-3, which is a human-derived breast cancer cell, was used. $IT_{50}$ was also calculated. $IT_{50}$ indicates the half of time required for attaining the drug concentration at which all of the cells die, and can be easily calculated based on the survival curve obtained by plotting the percentage of cell viability to the time axis. Table 4 shows the results.

TABLE 4

| Drug name | $IC_{50}$ (nM) | $IT_{50}$ (h) |
|---|---|---|
| PTX | 5.91 | 15.9 |
| gPTX | 46.0 | 18.7 |
| gPTX-L | 47.8 | 17.2 |
| gPTX-IL | 22.1 | 5.2 |

The results shown in Table 4 indicated that regarding $IC_{50}$, the gPTX and gPTX-L showed no particular difference in the effect of killing breast cancer cells. In contrast, the results indicated that the gPTX-IL had a high effect of killing breast cancer cells compared to the gPTX and gPTX-L. The PTX showed the highest effect of killing breast cancer cells; however, considering the individual administration of drugs, it was difficult to assertively deliver a drug to a cancer cell whose demise was desired, and even if the PTX exhibited excellent anti-cancer effects, there was a high possibility that the drug is delivered to a site that is not targeted. Thus, side effects will inevitably occur; the PTX did not solve the conventional problem.

Regarding $IT_{50}$, the PTX, gPTX, and gPTX-L showed no difference in the time required for killing all (100%) of the cells. The results clearly indicated that the gPTX-IL exhibited about ⅓ of $IT_{50}$ compared to the above three. Specifically, the results indicated that the gPTX-IL killed cells within an extremely short period of time compared to the other three. This is presumably because the gPTX-IL was assertively delivered to and encapsulated in the breast cancer cells, and high anti-cancer effects were exhibited by the PTX per se. Therefore, it was obvious that the gPTX-IL exhibited an excellent DDS effect on breast cancer cells.

Test Example 4: Acute Toxicity Study gPTX, gPTX-L, or a solvent control (Cremophor:ethanol:ultra-pure water=12:12:76; volume ratio) was administered via tail vein to each BALB/c mouse (female, 5 weeks old) five times with intervals of 1 hour (N=3). The dose per each was 200 µl/20 g. The total dose of gPTX was 200 mg/kg. Observation over time was performed during and after the administration. FIG. 1 shows the results.

The results confirmed that, in the gPTX administration group, almost all of the mice were dead by the third administration; however, in the gPTX-L (liposome encapsulating gPTX) administration group and the control group, almost the same number of mice survived. This indicated that to enhance anti-cancer effects, gPTX-L, i.e., a liposome encapsulating gPTX, can be administered in a larger amount than conventional gPTX.

Test Example 5: Cell Observation

Figure 2:
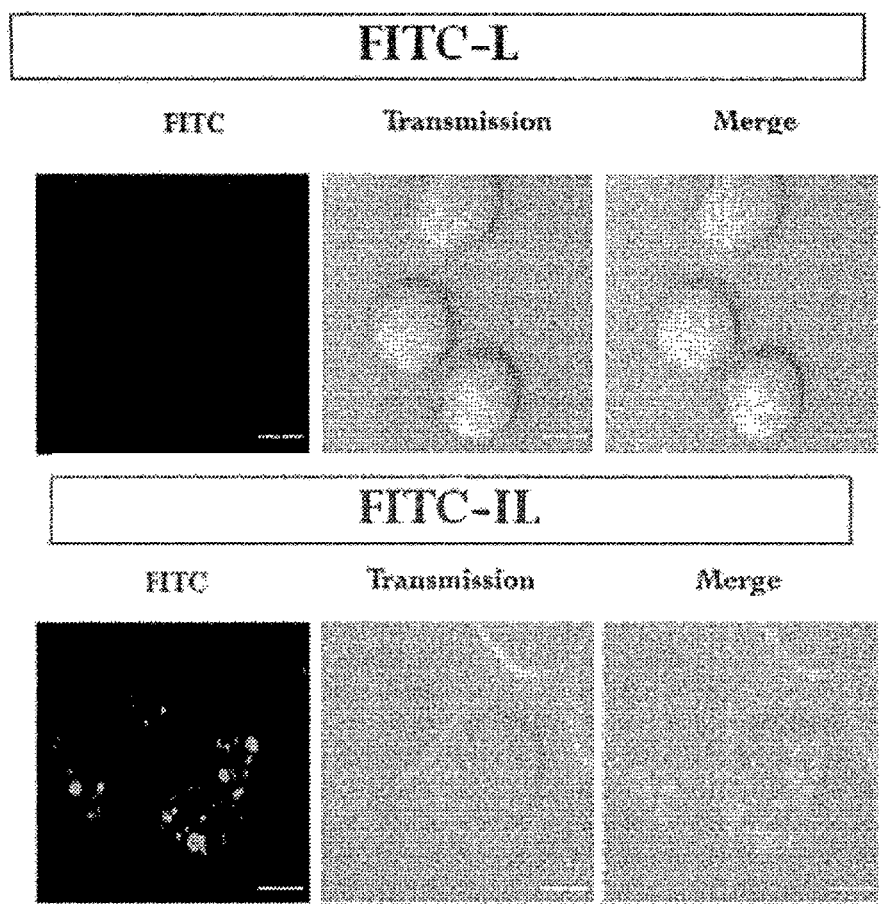
FIG. 2 shows fluorography images indicating the accumulation of the liposome encapsulating a paclitaxel monoglycoside, and carrying an antibody recognizing a breast cancer cell on the breast cancer cell, the liposome being obtained by the production method of the present invention in Test Example 5. The bar in each image indicates 10 μm.
Figure 3:
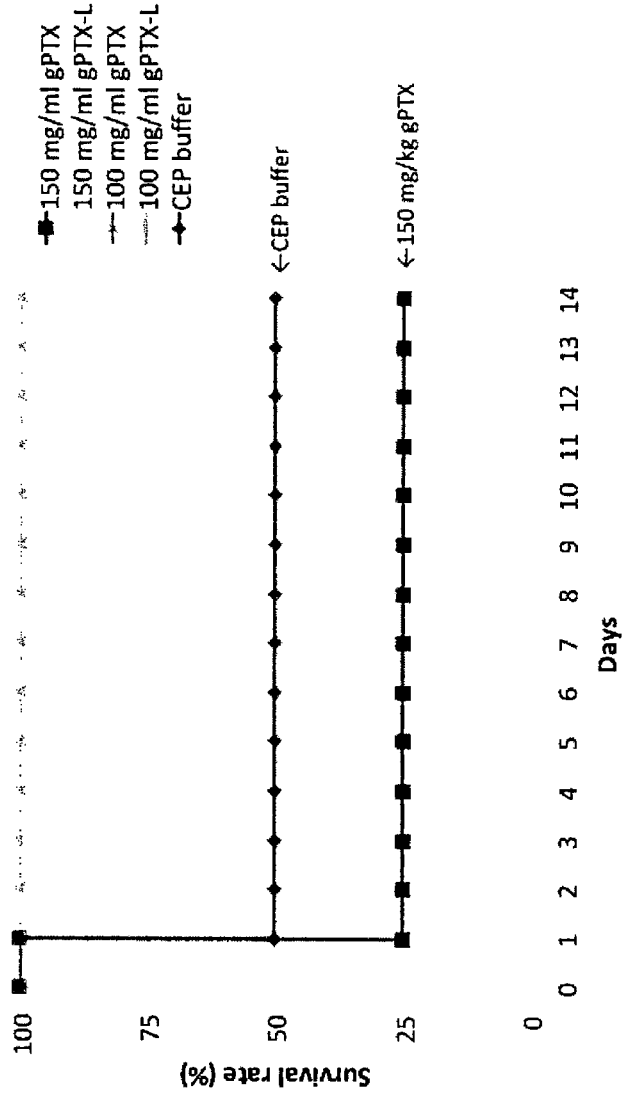
FIG. 3 shows the acute toxicity study results in Test Example 8. In the graph, the vertical axis shows the survival rate, and the horizontal axis shows the days after administration.
Figure 4:
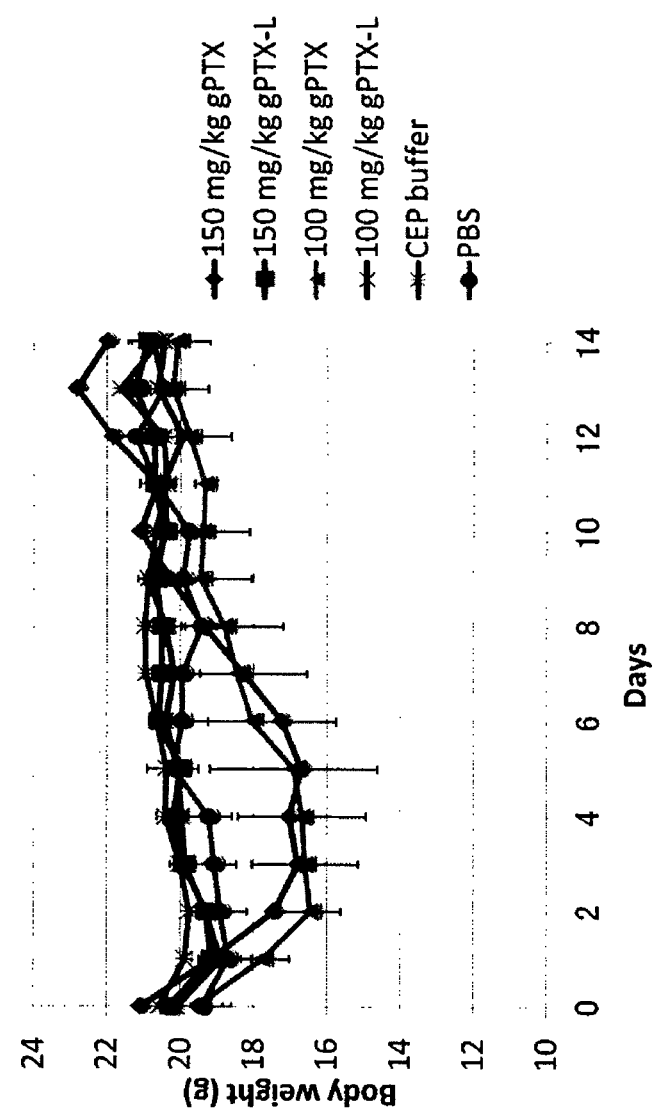
FIG. 4 shows the acute toxicity study results in Test Example 8. In the graph, the vertical axis shows the body weight, and the horizontal axis shows the days after administration.

A liposome encapsulating FITC (lipid composition being the same as above, hereinafter referred to as FITC-L), or a liposome having trastuzumab prepared by the same method as above (lipid composition being the same as above, hereinafter referred to as FITC-IL) affected on a SK-BR-3 cell, which is a human-derived breast cancer cell, and incubated for two hours. Thereafter, the cells were observed according to a known method using fluorescence microscopy. FIG. 2 shows the results.

FIG. 2 indicates that FITC-L did not accumulate on the cell, whereas FITC-IL accumulated on the cell and was encapsulated in the cell. This revealed that the liposome having trastuzumab was bound to HER2 expressed on the surface of the SK-BR-3 cell, and also encapsulated in the cell.

Test Example 6: Preparation and Modification Method of Liposome Encapsulating gPTX (Examination of Liposome Lipid Composition)

DPPC was weighed in an amount of 13.2, 10.6, or 8.8 mg, cholesterol was weighed in an amount of 2.1, 3.7, or 4.6 mg, and mPEG-DSPE was weighed in an amount of 2.1 mg. These components were mixed in a 50 ml eggplant flask. The mixed lipid was dissolved in an organic solvent (chloroform:methanol=9:1; volume ratio) (3 ml), and five-minute sonication was performed using a bath sonicator. Thereafter, the mixture was dried using a rotary evaporator, and then vacuum-dried overnight to completely remove the solvent, thus preparing a lipid film.

Subsequently, after the eggplant flask was immersed in a hot bath at 60° C. for 5 minutes, a CEP buffer (Cremophor EL:ethanol:PBS (PH 7.4)=12:12:76; volume ratio) (1 ml) was added thereto to dissolve the lipid film, thus preparing a multilamellar vesicle (MLV). The MLV was subjected to five-minute sonication to thereby prepare a small lamellar vesicle (SLV). To remove an unencapsulated buffer and free lipid, ultrafiltration (Amicon Ultra 100K membrane (Millipore)) was performed.

The 1 mg/ml gPTX solution (solvent: 40% EG-containing PBS (pH 7.4)) (1 ml) was added to the prepared liposome, and the mixture was immersed in a hot bath at 60° C. for 15 minutes. To remove an unencapsulated drug solution, ultrafiltration (Amicon Ultra 100K membrane (Millipore)) was performed. The above operation was performed another two times to encapsulate the drug. After the encapsulation, PBS washing was performed to completely remove the unencapsulated drug solution.

Regarding the efficiency of paclitaxel monoglycoside encapsulated in the obtained liposome, the encapsulated drug amount and the particle size were measured and calculated by the same method as in Test Example 2. Table 5 shows the results.

TABLE 5

| | | | Particle size (nm) | |
|---|---|---|---|---|
| DPPC:Chol | EE (%) | LE (%) | Before encapsulation | After encapsulation |
| 3:1 | 62.7 | 7.1 | 131.1 | 121.9 |
| 3:2 | 64.1 | 7.3 | 165.2 | 169.4 |
| 3:3 | 61.0 | 6.9 | 170.7 | 245.0 |

As shown in Table 5, in all of the cases where the weight ratios of DPPC:Chol (cholesterol) were 3:1, 3:2, and 3:3, the encapsulation efficiency was extremely high, such as 60% or more. When the weight ratio of DPPC:Chol was 3:1 or 3:2, the average particle size was not changed even after gPTX encapsulation.

Further, the leakage of gPTX from the obtained liposome encapsulating gPTX was examined, and the results revealed that the most excellent gPTX-carrying and gPTX-retaining effects were exhibited when the weight ratio of DPPC:Chol was 3:1 (data not shown).

Test Example 7: Method for Preparing and Modifying Liposome Encapsulating gPTX (Examination of Incubation Time)

In the experiment shown in Test Example 6, the encapsulation efficiency wherein the material quantity ratio of DPPC:Chol was 3:1 was obtained by changing the incubation time to 5, 10, 30, and 60 minutes. The measurement and calculation was performed by the same method as in Test Example 2 above. Table 6 shows the results.

TABLE 6

| Incubation time | 5 min | 15 min | 30 min | 60 min |
|---|---|---|---|---|
| EE | 34.9 | 72.9 | 62.3 | 26.8 |

The results of Table 6 revealed that gPTX was most efficiently encapsulated in the liposome when the incubation time was 15 minutes.

Test Example 8: Acute Toxicity Study Using Liposome Encapsulating gPTX Obtained by Modification Method Acute toxicity study was performed using the liposome encapsulating gPTX (gPTX-L) obtained in Test Example 7.

Specifically, gPTX, gPTX-L, a CEP buffer (Cremophor: ethanol:ultra-pure water=12:12:76; volume ratio), or PBS was administered via tail vein to each BALB/c mouse (female, 6 weeks old) two times with an interval of three hours (N=4). The dose per each was 200 μl/20 g. The total dose of gPTX was 150 or 100 mg/kg in view of gPTX. Observation over time was performed during and after the administration. FIG. 3 shows the results.

As shown in FIG. 3, in the group in which the gPTX was administered in a total amount of 150 mg/kg, three mice were dead one day after the administration. In the group in which the CEP buffer was administered, two mice were dead one day after the administration. In contrast, in the group in which the gPTX-L was administered in a total gPTX amount of 150 mg/kg, the survival rate was 100% over 14 days as in the PBS administration group.

Subsequently, the body weight change in each treated group was measured (FIG. 4). In the gPTX administration group, a significant body weight loss was observed; however, in the gPTX-L administration group where the total amount of gPTX administered was the same as that in the gPTX group, a body weight shift similar to that of the PBS administration group was observed. The results indicated that the liposome encapsulating gPTX exhibited high safety compared to the gPTX.

Test Example 9: Cell Delivery Experiment Using Liposome Encapsulating gPTX Obtained by Modification Method 3 mg/ml MAL-PEG-DSPE (470 μl) dissolved in PBS was added to the liposome encapsulating gPTX (gPTX-L), and the mixture was immersed in a hot bath at 50° C. for 10 minutes.

At the same time, an antibody to be bound to the liposome was prepared. A 2-iminothiolane solution (500 nmol) was added to a trastuzumab solution (1.5 mg) dissolved in a HEPES buffer (25 mM HEPES, 140 mM NaCl, pH 8.0), and the mixture was reacted for one hour at room temperature in the dark to introduce a SH group to the trastuzumab. Using a Sephadex G-25 column, unreacted compound were removed from the reacted solution, and the buffer was changed to PBS.

Subsequently, the trastuzumab solution containing the SH group was mixed with the liposome solution, and the mixture was stirred at 4° C. overnight to bind the trastuzumab to the liposome. To remove unreacted trastuzumab, ultrafiltration (Vivaspin 2 300K membrane (Sartorius)) was performed. A liposome (gPTX-IL) having the antibody and encapsulating gPTX was thus obtained.

To prepare a liposome as a control, 470 μl of 3 mg/ml mPEG-DSPE was added to the liposome solution, and the mixture was stirred in a hot bath at 50° C. for 10 minutes. Thereafter, ultrafiltration (Anicon Ultra 100K membrane (produced by Millipore)) was performed.

In the same manner as in Test Example 3, anti-cancer activity was measured. SK-BR-3, which is a human-derived breast cancer cell, and HT-29, which is a colon adenocarcinoma cell, were used. Specifically, cells were seeded to a 96 well-plate at 5000 cells/well, and incubated for 24 hours. Then, PTX, gPTX, gPTX-L, and gPTX-IL were separately added at different concentrations, followed by incubation.

72 hours later, the percentage of cell viability was calculated by an MTT assay. First, the concentration ($IC_{50}$) at which 50% of the cells die was obtained from the survival curve. Subsequently, the time ($IT_{50}$) at which 50% of the cells die was obtained from the survival curve. After the cells were seeded, PTX, gPTX, gPTX-L, or gPTX-IL was added at a concentration attaining $IC_{100}$, which was obtained from the survival curve. Incubation was then performed for 1, 2, 6, 12, 24, 48, or 72 hours, and then medium exchange was performed. 72 hours after the drug addition, the MTT assay was performed in the same manner as in the above experiment to obtain the survival rate, and calculate the $IT_{50}$ therefrom. Tables 7 and 8 show the results.

TABLE 7

| Drug name | HT-29 | | SK-BR3 | |
| --- | --- | --- | --- | --- |
| | $IC_{50}$ | $IC_{100}$ | $IC_{50}$ | $IC_{100}$ |
| PTX | 1.3 ± 0.5 | 10 | 5.5 ± 1.3 | 30 |
| gPTX | 11.0 ± 0.8 | 50 | 18.9 ± 1.1 | 100 |
| gPTX-L | 1.3 ± 0.5 | 30 | 6.6 ± 0.9 | 30 |
| gPTX-IL | 1.3 ± 0.5 | 30 | 5.3 ± 0.7 | 30 |

* $IC_{50}$ and $IC_{100}$ are both in nM.

The results of $IC_{50}$ and $IC_{100}$ shown in Table 7 revealed that all of the PTX, gPTX, gPTX-L, and gPTX-IL exhibited remarkably excellent anti-cancer activities on breast cancer cells and colon cancer cells. Further, the comparison of gPTX and PTX revealed that although the anti-cancer activity weakened due to the binding of a sugar chain to the PTX, the gPTX exhibited an anti-cancer activity similar to that of the PTX when encapsulated in the liposome (see gPTX-L and gPTX-IL). However, there was no particular difference in anti-cancer activity between the gPTX-L and gPTX-IL. Specifically, the results indicated that the anti-cancer activity was not especially changed in the presence or absence of the antibody.

TABLE 8

| Drug name | $IT_{50}$ (h) | |
| --- | --- | --- |
| | HT-29 | SK-BR-3 |
| PTX | 11.9 | 9.8 |
| gPTX | 9.6 | 8.3 |
| gPTX-L | 2.3 | 3.6 |
| gPTX-IL | 1.1 | 1.6 |

The results of $IT_{50}$ shown in Table 8 revealed that the gPTX-IL had lower $IT_{50}$ than the gPTX-L. This indicated that the time required for killing cancer cells was short, and that the PTX was efficiently delivered to cancer cells in a short period of time, thus making it possible to rapidly kill the cancer cells.

Test Example 10: In Vivo Delivery Experiment of Liposome Having Antibody

Subsequently, to examine the in vivo delivery of a liposome having an antibody to a tumor tissue in an experiment, a liposome having an antibody encapsulating a fluorescent dye was prepared. Specifically, human serum albumin (HSA) (10 mg) was dissolved in a 0.1 M sodium carbonate buffer (pH 9.3, 1 ml) to obtain a 10 mg/ml HSA solution. The 10 mg/ml HSA solution (1 ml) was dissolved in Cy5.5 monofunctional dye (one vial). After the resultant was stirred at room temperature for 30 minutes, an unreacted product was removed using a Sephadex G-25 column to collect Cy5.5-binding HSA (HSA-Cy5.5).

The lipid film was prepared according to the above test example, and immersed in a hot bath at 60° C. for five minutes. Thereafter, the HSA-Cy 5.5 solution was added to dissolve the lipid film. While the solution was immersed in a hot bath at 60° C., sonication was performed for three minutes. To remove unencapsulated HSA-Cy5.5, ultrafiltration (Amicon Ultra 100K membrane (produced by Millipore) was performed. Thereafter, an antibody (Trastuzumab) was bound to the obtained liposome using the method shown in Test Example 8.

Figure 5:
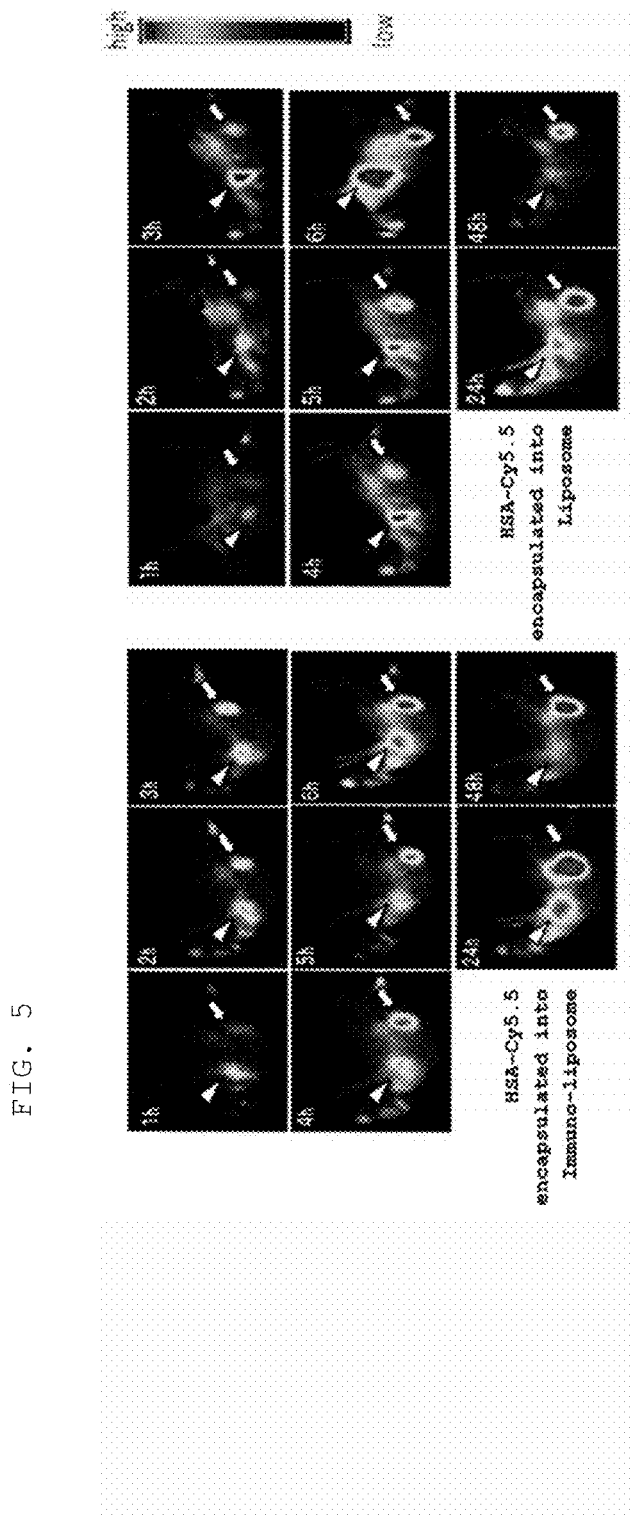
FIG. 5 shows the in vivo delivery experimental results in Test Example 10. The left side of the figure shows the accumulation position and degree obtained after the liposome encapsulating HSA labeled with Cy5.5 and having the antibody was administered to each mouse via tail vein, and the right side of the figure shows the accumulation position and degree obtained after the liposome encapsulating HSA labeled with Cy5.5 and having no antibody was administered to each mouse via tail vein. In each image, the arrow indicates a tumor, and the triangle indicates a liver.
Figure 6:
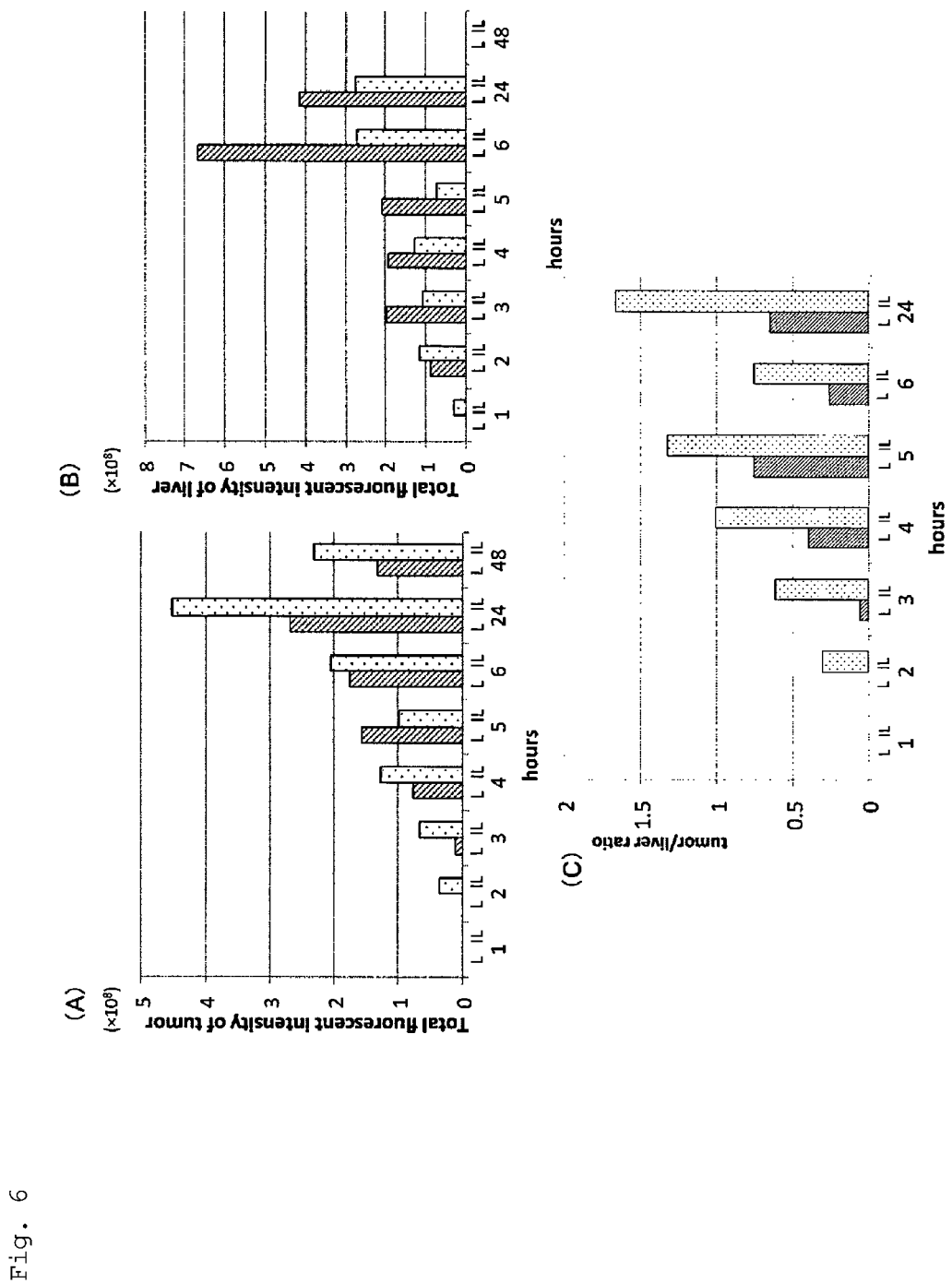
FIG. 6 shows graphs of the imaging results shown in FIG. 5. (A) shows the results of tumor tissue, (B) shows the results of liver, and (C) shows the results in which the accumulation degree in the tumor tissue relative to the liver was quantified as a ratio. In the quantifying, the tumor and liver sites were selected according to the threshold value to measure total fluorescence intensity. Specifically, Digital Microscopy Software Slide Book 4.2 (produced by Nippon Roper) was used.

HT-29 cells were subcutaneously administered to each ICR-nu/nu mouse (male, 5 weeks old) at $3.0 \times 10^6$ cells, followed by the administration of the liposome having an antibody and encapsulating HSA-Cy 5.5. In a comparative experiment, a liposome encapsulating HSA-Cy5.5 and having no antibody was administered. When the tumor volume attained about 100 $mm^3$, the liposome encapsulating HSA-Cy5.5 (L) or the liposome having an antibody (IL) was administered via tail vein. Cy5.5 fluorescence was photographed using a CCD camera (in vivo Macro Imaging System I.C.E.) after 1, 2, 3, 4, 5, 6, 24, and 48 hours from the administration (excitation light 650 nm/fluorescence wavelength 710 nm). FIGS. 5 and 6 show the results.

The results shown in FIG. 5 indicated that the liposome accumulated on the tumor by the EPR effect regardless of the presence or absence of the antibody. However, the results revealed that the liposome having an antibody more efficiently accumulated on the tumor tissue, and accumulated less on the liver.

The results shown in FIG. 6 clearly indicated that the liposome having an antibody always accumulated on the tumor tissue in a larger amount than the liposome having no antibody, whereas the liposome having no antibody always accumulated on the liver tissue in a large amount. Further, unlike the liposome having an antibody, the liposome having no antibody did not accumulate on the tumor cell 48 hours after the administration.

Test Example 11: In Vivo Anti-Cancer Activity Experiment of Liposome Encapsulating gPTX and Having Antibody HT-29 cells were subcutaneously administered at $3.0 \times 10^6$ cells to each ICR-nu/nu mouse (male, 5 weeks old). When the tumor volume became about 50 to 200 $mm^3$, the above gPTX, the gPTX-L produced in Test Example 7, the gPTX-IL produced in Test Example 9, trastuzumab, the liposome (empty L) encapsulating no gPTX and having no antibody (trastuzumab) produced in Test Example 9, the liposome (empty IL) encapsulating gPTX-L and having an antibody (trastuzumab) produced in Test Example 9, a CEP buffer, or PBS was administered via tail vein two times at an interval of 3 hours (N=4). The dose per each was 200 μl/20 g. The total dose of gPTX was 150 mg/kg, and the total dose of trastuzumab was 200 mg/kg. The tumor volume shift after administration was observed. The figure shows the results. The tumor volume was calculated from the formula (3) below.

Tumor volume=(tumor smallest $diameter^2$×tumor longest diameter)/2    (3)

The body weight shift and the survival rate in each group were measured. FIGS. 6 to 9 show the results.

The results shown in FIG. 6 revealed that the gPTX-IL exhibited a remarkably excellent anti-tumor growth inhibition effect as in the gPTX. In contrast, almost no tumor growth inhibition effect was observed in the other administration groups.

Figure 7:
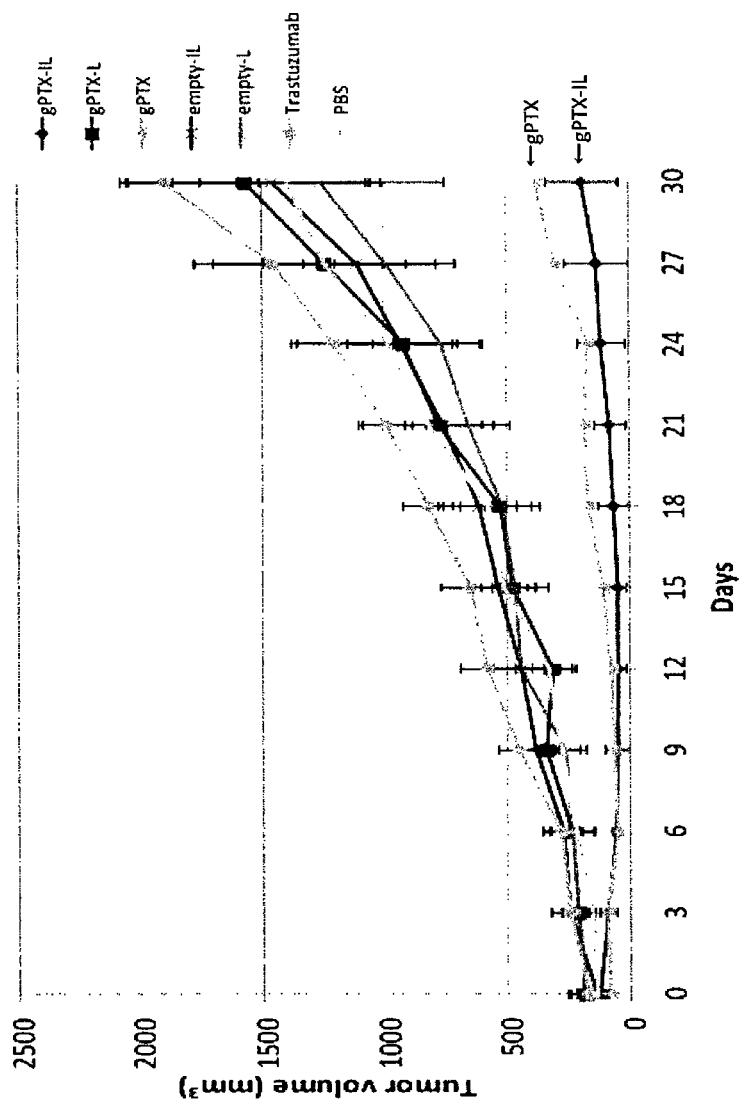
FIG. 7 shows the in vivo anti-cancer activity experimental results in Test Example 11. In the graph, the vertical axis indicates the tumor volume, and the horizontal axis indicates the days after administration.
Figure 8:
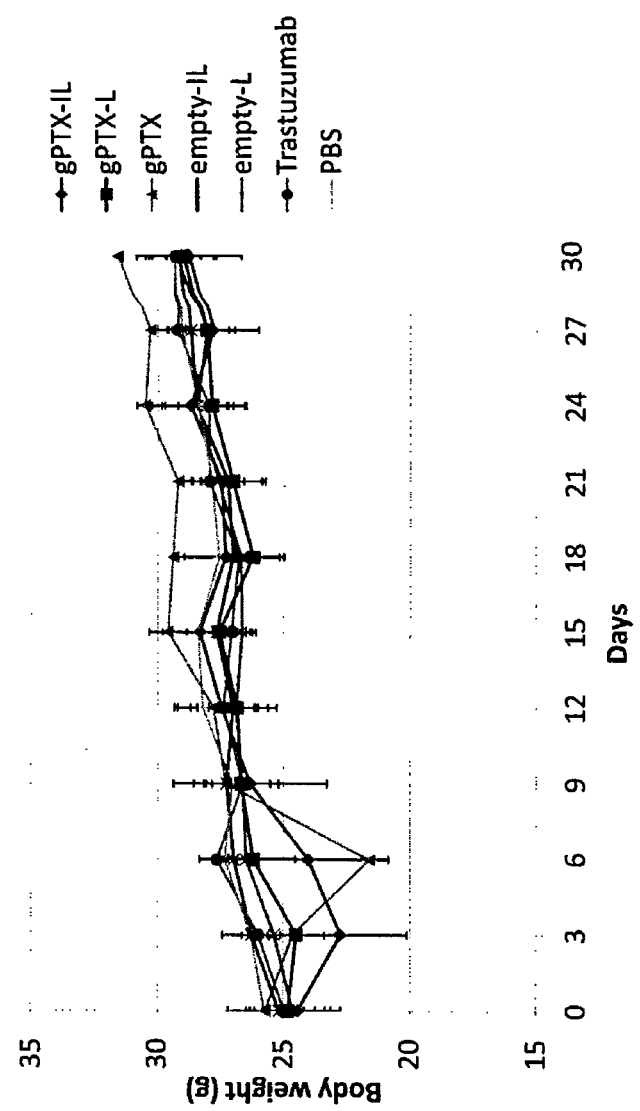
FIG. 8 shows the in vivo anti-cancer activity experimental results in Test Example 11. In the graph, the vertical axis shows the body weight, and the horizontal axis shows the days after administration.
Figure 9:
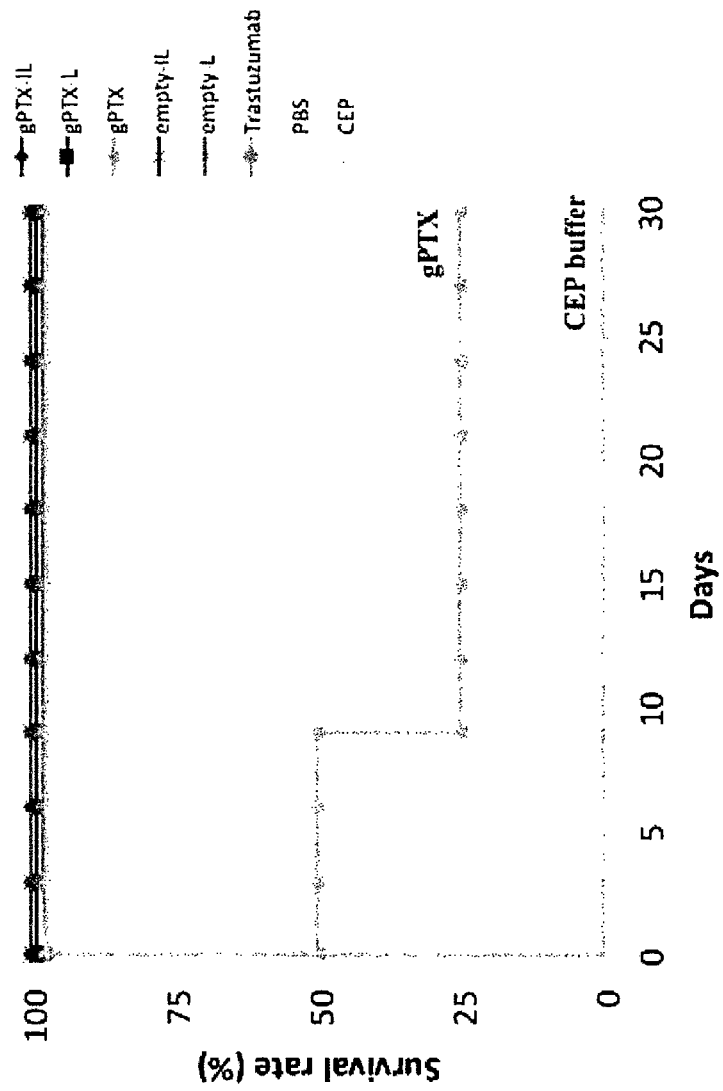
FIG. 9 shows the in vivo anti-cancer activity experimental results in Test Example 11. In the graph, the vertical axis indicates the survival rate, and the horizontal axis indicates the days after administration.

From the results shown in FIG. 7, although a body weight loss was observed after the administration of gPTX-IL, the loss was recovered; consequentially, a weight shift similar to that in the other administration groups was observed.

In the CEP administration group, all mice died in three hours after the administration; and in the gPTX administration group, two mice died in three hours after the administration, and one died one week after the administration. In FIG. 7 showing the body weight shift, the remarkable body weight loss in the gPTX administration group was due to the dead mice.

Figure 10:
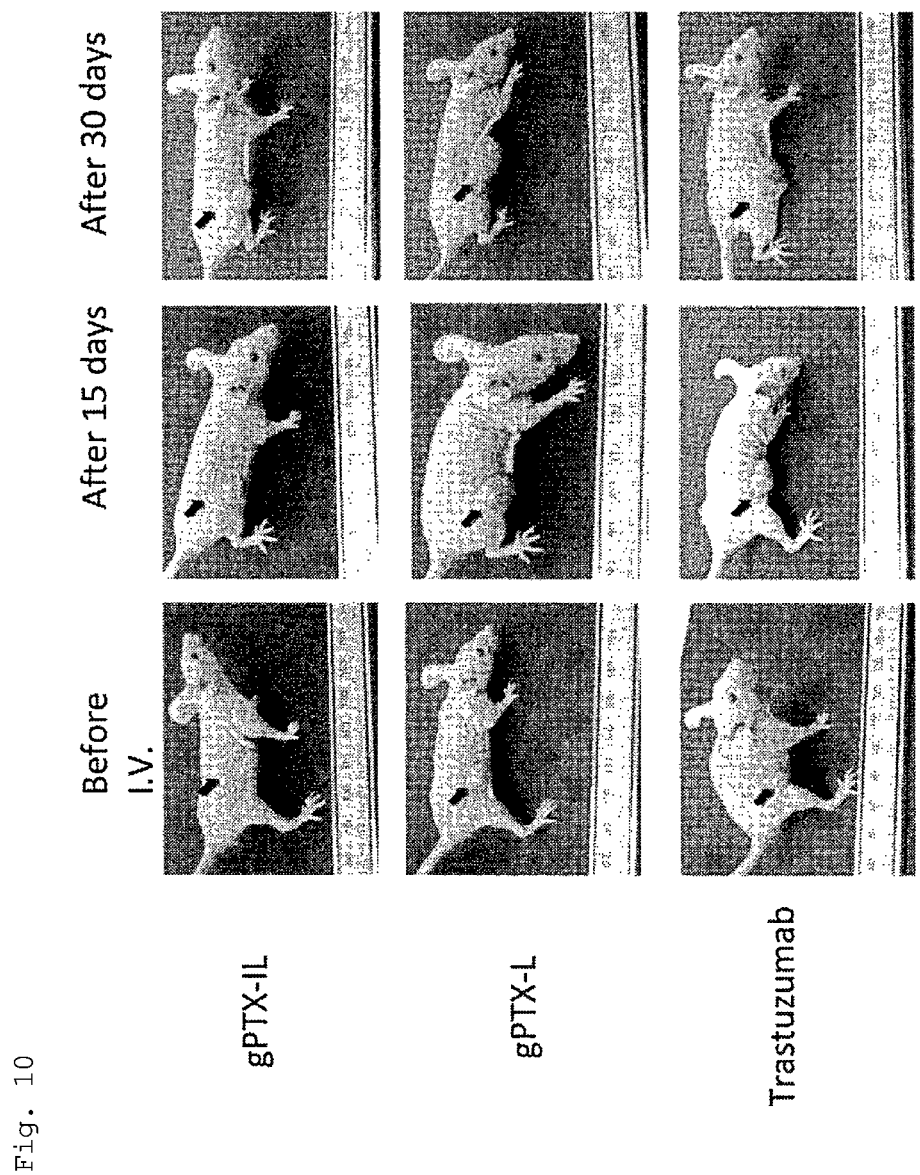
FIG. 10 shows photo images of mice in Test Example 11. In each image, the arrow indicates a tumor.

The photographs shown in FIG. 10 clearly indicate tumor growth effects.

In view of the above, it was revealed that the liposome encapsulating gPTX and having trastuzumab, which is a monoclonal antibody specifically recognizing Her2, exhibits an effect of remarkably inhibiting the growth of a tumor tissue in a colon cancer-derived HT-29 bearing mice. It was also revealed that such a liposome has remarkably low side effects because body weight was not lost by administration, and the fatality rate was low. Thus, the liposome was revealed to be useful as a liposome formulation exhibiting a remarkably excellent effect on a cancer cell.

The invention claimed is:

1. A method for producing a liposome encapsulating a paclitaxel monoglucoside and/or a docetaxel monoglucoside, and having an antibody specifically recognizing a cancer cell, the method comprising a step of bringing a liposome encapsulating a polyoxyethylene ester derivative, a lower alcohol, and a buffer or water into contact with a solution in which a paclitaxel monoglucoside and/or a docetaxel monoglucoside is dissolved in an alkylene glycol-containing buffer or water, wherein the liposome contains 3 parts by weight dipalmitoylphosphatidylcholine (DPPC) to 0.5-3 parts by weight cholesterol.

2. The method according to claim 1, wherein the polyoxyethylene ester derivative is polyoxyethylene castor oil ester.

3. The method according to claim 1, wherein the contact time is 10 to 40 minutes.

4. The method according to claim 1, wherein the cancer cell is a breast cancer cell.

5. The method according to claim 1, wherein the antibody specifically binds to HER2 protein.

6. A liposome formulation comprising liposomes encapsulating a liquid solution of paclitaxel monoglucoside and/or docetaxel monoglucoside, and an antibody specifically recognizing a cancer cell bound thereto, wherein the liquid solution is a mixed solvent consisting of polyoxyethylene castor oil ester, $C_{1-4}$ alcohol, and a buffer or water, in which paclitaxel monoglucoside and/or docetaxel monoglucoside is dissolved, and wherein the liposomes contain 3 parts by weight DPPC to 0.5-3 parts by weight cholesterol.

7. The liposome formulation according to claim 6, wherein the mol of the paclitaxel of monoglucoside of total lipids of the liposome is 1.0 to $15.0 \times 10^{-2}$.

8. The liposome formulation according to claim 6, wherein the cancer cell is a breast cancer cell.

9. The liposome formulation according to claim 6, wherein the antibody specifically binds to HER2 protein.

* * * * *